(12) United States Patent
Wong et al.

(10) Patent No.: US 11,213,570 B2
(45) Date of Patent: Jan. 4, 2022

(54) USE OF C1Q/TNF-RELATED PROTEIN-1 (CTRP1) TO TREAT FATTY LIVER DISEASE

(71) Applicant: THE JOHNS HOPKINS UNIVERSITY, Baltimore, MD (US)

(72) Inventors: Guang William Wong, Lutherville, MD (US); Susana Rodriguez, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/307,241

(22) PCT Filed: Jun. 8, 2017

(86) PCT No.: PCT/US2017/036535
§ 371 (c)(1),
(2) Date: Dec. 5, 2018

(87) PCT Pub. No.: WO2017/214383
PCT Pub. Date: Dec. 14, 2017

(65) Prior Publication Data
US 2019/0191676 A1    Jun. 27, 2019

Related U.S. Application Data

(60) Provisional application No. 62/348,189, filed on Jun. 10, 2016.

(51) Int. Cl.
| | | |
|---|---|---|
| A61K 38/17 | (2006.01) | |
| A61K 38/19 | (2006.01) | |
| A61P 1/16 | (2006.01) | |
| A61K 31/4402 | (2006.01) | |
| A01K 67/027 | (2006.01) | |

(52) U.S. Cl.
CPC .......... *A61K 38/19* (2013.01); *A61K 31/4402* (2013.01); *A61K 38/1709* (2013.01); *A61K 38/1719* (2013.01); *A61P 1/16* (2018.01); *A01K 67/027* (2013.01); *A01K 67/0276* (2013.01); *A01K 2207/25* (2013.01); *A01K 2217/075* (2013.01); *A01K 2227/105* (2013.01); *A01K 2267/0362* (2013.01)

(58) Field of Classification Search
CPC .. A61K 31/427; A61K 38/00; A61K 38/1709; A61K 38/191; A61K 38/2006; A61K 38/22; A61P 1/16
See application file for complete search history.

(56) References Cited

U.S. PATENT DOCUMENTS

| | | | |
|---|---|---|---|
| 9,872,844 B2 * | 1/2018 | Zemel | A61K 31/519 |
| 2016/0017019 A1 * | 1/2016 | Ilan | C12N 15/8258 424/134.1 |
| 2018/0066048 A1 * | 3/2018 | Moodie | C07K 16/241 |
| 2018/0243347 A1 * | 8/2018 | Agrawal | A61P 37/06 |

FOREIGN PATENT DOCUMENTS

WO    2014150772 A1    9/2014

OTHER PUBLICATIONS

S. Harrison. New Treatments for Nonalcoholic Fatty Liver Disease. Current Gastroenterology Reports. 2006, vol. 8, pp. 21-29. (Year: 2006).*
Yu, et al., The effect of thiazolidinediones on plasma adiponectin levels in normal, obese, and type 2 diabetic subjects. Diabetes. Oct. 2002;51(10):2968-74.
Kubota, et al., Adiponectin-dependent and -independent pathways in insulin-sensitizing and antidiabetic actions of thiazolidinediones. Diabetes. Dec. 2006;55(Supp 2):S32-38.
Hundal, et al., Mechanism by which metformin reduces glucose production in type 2 diabetes. Diabetes. Dec. 2000;49(12):2063-9.
Fujita, et al., Effects of antidiabetic treatment with metformin and insulin on serum and adipose tissue adiponectin levels in db /db mice. Endocr J. Aug. 2005;52(4):427-33.
Gale, et al., Diabetes and gender. Diabetologia. Jan. 2001;44(1):3-15.
O'Rahilly, et al., Genetic factors in type 2 diabetes: the end of the beginning? Science. Jan. 21, 2005;307(5708):370-3.
Tomas, et al., Enhanced muscle fat oxidation and glucose transport by ACRP30 globular domain: acetyl-CoA carboxylase inhibition and AMP-activated protein kinase activation. Proc Natl Acad Sci U S A. Dec. 10, 2002;99(25):16309-13.
Pajvani, et al., Complex distribution, not absolute amount of adiponectin, correlates with thiazolidinedione-mediated improvement in insulin sensitivity. J Biol Chem. Mar. 26, 2004;279(13):12152-62.
Takamatsu, et al., Hibernation associated gene regulation of plasma proteins with a collagen-like domain in mammalian hibernators. Mol Cell Biol. Mar. 1993;13(3):1516-21.
Vitagliano, et al., Structural bases of collagen stabilization induced by proline hydroxylation. Biopolymers. Apr. 15, 2001;58(5):459-64.
Chu, et al., Sequence analysis of α1(VI) and α2(VI) chains of human type VI collagen reveals internal triplication of globular domains similar to the A domains of von Willebrand factor and two α2(VI) chain variants that differ in the carboxy terminus. EMBO J. Aug. 1989;8(7):1939-1946.
Stokes, et al., Human α3(VI) collagen gene. Characterization of exons coding for the amino-terminal globular domain and alternative splicing in normal and tumor cells. J Biol Chem. Jun. 1991;266(13):8626-8633.
Bell, et al., Enzymes of glycerolipid synthesis in eukaryotes. Annu Rev Biochem. 1980;49:459-87.

(Continued)

*Primary Examiner* — Jeffrey E. Russel
(74) *Attorney, Agent, or Firm* — Johns Hopkins Technology Ventures

(57) ABSTRACT

Methods for the treatment or prevention of disease, such as fatty liver disease and obesity, are described including the modulation the amount of CTRP1 in a subject. Novel mouse strains are also described.

1 Claim, 20 Drawing Sheets
Specification includes a Sequence Listing.

(56) References Cited

OTHER PUBLICATIONS

Butler, et al., A recurring problem with the analysis of energy expenditure in genetic models expressing lean and obese phenotypes. Diabetes. Feb. 2010;59(2):323-9.

Byerly, et al., C1q/TNF-related Protein 4 (CTRP4) Is a Unique Secreted Protein with Two Tandem C1q Domains That Functions in the Hypothalamus to Modulate Food Intake and Body Weight. J Biol Chem. Feb. 14, 2014;289(7):4055-69.

Byerly, et al., A central role for C1q/TNF-related protein 13 (CTRP13) in modulating food intake and body weight. PLoS One. Apr. 25, 2013;8(4):e62862.

Cacho, et al., Validation of simple indexes to assess insulin sensitivity during pregnancy in Wistar and Sprague-Dawley rats. Am J Physiol Endocrinol Metab. Nov. 2008;295(5):E1269-76.

Chalupova, et al., Development of a novel enzyme-linked immunosorbent assay (ELISA) for measurement of serum CTRP1: a pilot study: measurement of serum CTRP1 in healthy donors and patients with metabolic syndrome. Clin Biochem. Jan. 2013;46(1-2):73-8.

Ding, et al., Sex hormone-binding globulin and risk of type 2 diabetes in women and men. N Engl J Med. Sep. 17, 2009;361(12):1152-63.

Enomoto, et al., Adipolin/C1qdc2/CTRP12 functions as an adipokine that improves glucose metabolism. J Biol Chem. Oct. 7, 2011;286(40):34552-8.

Gui, et al., Sexual dimorphism and regulation of resistin, adiponectin, and leptin expression in the mouse. Obes Res. Sep. 2004;12(9):1481-91.

Han, et al., CTRP1 protects against diet-induced hyperglycemia by enhancing glycolysis and fatty acid oxidation. J Nutr Biochem. Jan. 2016;27:43-52.

Harman-Boehm, et al., Macrophage infiltration into omental versus subcutaneous fat across different populations: effect of regional adiposity and the comorbidities of obesity. J Clin Endocrinol Metab. Jun. 2007;92(6):2240-7.

Hotamisligil, Inflammation and metabolic disorders. Nature. Dec. 14, 2006;444(7121):860-7.

Huang, et al., The GLUT4 glucose transporter. Cell Metab. Apr. 2007;5(4):237-52.

Jeon, et al., A novel adipokine CTRP1 stimulates aldosterone production. FASEB J. May 2008;22(5):1502-11.

Kadowaki, et al., Adiponectin and adiponectin receptors in insulin resistance, diabetes, and the metabolic syndrome. J Clin Invest. Jul. 2006;116(7):1784-92.

Kahn, et al., AMP-activated protein kinase: ancient energy gauge provides clues to modern understanding of metabolism. Cell Metab. Jan. 2005;1(1):15-25.

Kambara, et al., CTRP9 protein protects against myocardial injury following ischemia-reperfusion through AMP-activated protein kinase (AMPK)-dependent mechanism. J Biol Chem. Jun. 1, 2012;287(23):18965-73.

Kambara, et al., C1q/Tumor Necrosis Factor-Related Protein 9 Protects against Acute Myocardial Injury through an Adiponectin Receptor I-AMPK-Dependent Mechanism. Mol Cell Biol. Jun. 2015;35(12):2173-85.

Kim, et al., Tumor necrosis factor-alpha and interleukin-1beta increases CTRP1 expression in adipose tissue. FEBS Lett. Jul. 10, 2006;580(16):3953-60.

Kubota, et al., Disruption of adiponectin causes insulin resistance and neointimal formation. J Biol Chem. Jul. 19, 2002;277(29):25863-6.

Lee, et al., Comparison between surrogate indexes of insulin sensitivity and resistance and hyperinsulinemic euglycemic clamp estimates in mice. Am J Physiol Endocrinol Metab. Feb. 2008;294(2):E261-70.

Lei, et al., Thromboxane synthase deficiency improves insulin action and attenuates adipose tissue fibrosis. Am J Physiol Endocrinol Metab. May 1, 2015;308(9):E792-804.

Livak, et al., Analysis of relative gene expression data using real-time quantitative PCR and the 2(-Delta Delta C(T)) Method. Methods. Dec. 2001;25(4):402-8.

Lu, et al., C1q/TNF-related protein-1: an adipokine marking and promoting atherosclerosis. Eur Heart J. Jun. 7, 2016;37(22):1762-71.

Ma, et al., Increased beta-oxidation but no insulin resistance or glucose intolerance in mice lacking adiponectin. J Biol Chem. Sep. 20, 2002;277(38):34658-61.

Maeda, et al., Diet-induced insulin resistance in mice lacking adiponectin/ACRP30. Nat Med. Jul. 2002;8(7):731-7.

Matthews, et al., Homeostasis model assessment: insulin resistance and beta-cell function from fasting plasma glucose and insulin concentrations in man. Diabetologia. Jul. 1985;28(7):412-9.

Mayes, et al., Direct effects of sex steroid hormones on adipose tissues and obesity. Obes Rev. Nov. 2004;5(4):197-216.

Millar, et al., Determining hepatic triglyceride production in mice: comparison of poloxamer 407 with Triton WR-1339. J Lipid Res. Sep. 2005;46(9):2023-8.

Miller, Why are sex and gender important to basic physiology and translational and individualized medicine? Am J Physiol Heart Circ Physiol. Mar. 2014;306(6):H781-8.

Murayama, et al., CTRP3 plays an important role in the development of collagen-induced arthritis in mice. Biochem Biophys Res Commun. Jan. 3, 2014;443(1):42-8.

Nawrocki, et al., Mice lacking adiponectin show decreased hepatic insulin sensitivity and reduced responsiveness to peroxisome proliferator-activated receptor gamma agonists. J Biol Chem. Feb. 3, 2006;281(5):2654-60.

Pan, et al., Circulating complement-C1q TNF-related protein 1 levels are increased in patients with type 2 diabetes and are associated with insulin sensitivity in Chinese subjects. PLoS One. May 14, 2014;9(5):e94478.

Peterson, et al., C1q/TNF-related protein-1 (CTRP1) enhances fatty acid oxidation via AMPK activation and ACC inhibition. J Biol Chem. Jan. 6, 2012;287(2):1576-1587.

Peterson, et al., CTRP2 overexpression improves insulin and lipid tolerance in diet-induced obese mice. PLoS One Feb. 20, 2014;9(2):e88535.

Peterson, et al., CTRP3 attenuates diet-induced hepatic steatosis by regulating triglyceride metabolism. Am J Physiol Gastrointest Liver Physiol. Aug. 1, 2013;305(3):G214-24.

Peterson, et al., CTRP9 transgenic mice are protected from diet-induced obesity and metabolic dysfunction. Am J Physiol Regul Integr Comp Physiol. Sep. 2013;305(5):R522-33.

Peterson, et al., C1q/TNF-related Protein-3 (CTRP3), a Novel Adipokine That Regulates Hepatic Glucose Output. J Biol Chem. Dec. 17, 2010;285(51):39691-701.

Schmid, et al., C1q/TNF-related protein-3 (CTRP-3) attenuates lipopolysaccharide (LPS)-induced systemic inflammation and adipose tissue Erk-1/-2 phosphorylation in mice in vivo. Biochem Biophys Res Commun. Sep. 12, 2014;452(1):8-13.

Seldin, et al., Myonectin (CTRP15), a novel myokine that links skeletal muscle to systemic lipid homeostasis. J Biol Chem. Apr. 6, 2012;287(15):11968-80.

Shen, et al., Increased serum level of CTRP1 is associated with low coronary collateralization in stable angina patients with chronic total occlusion. Int J Cardiol. Jun. 1, 2014;174(1):203-6.

Su, et al., Inhibition of CTRP9, a novel and cardiac-abundantly expressed cell survival molecule, by TNFalpha-initiated oxidative signaling contributes to exacerbated cardiac injury in diabetic mice. Basic Res Cardiol. Jan. 2013;108(1):315.

Sun, et al., Fibrosis and adipose tissue dysfunction. Cell Metab. Oct. 1, 2013;18(4):470-7.

Sun, et al., C1q/Tumor Necrosis Factor-Related Protein-9, a Novel Adipocyte-Derived Cytokine, Attenuates Adverse Remodeling in the Ischemic Mouse Heart via Protein Kinase A Activation. Circulation. Sep. 10, 2013;128(11 Suppl 1):S113-20.

Takeuchi, et al., Biochemistry, physiology, and genetics of GPAT, AGPAT, and lipin enzymes in triglyceride synthesis. Am J Physiol Endocrinol Metab. Jun. 2009;296(6):E1195-209.

(56) References Cited

OTHER PUBLICATIONS

Tilg, et al., Evolution of inflammation in nonalcoholic fatty liver disease: the multiple parallel hits hypothesis. Hepatology. Nov. 2010;52(5):1836-46.
Uemura, et al., Adipose-derived factor CTRP9 attenuates vascular smooth muscle cell proliferation and neointimal formation. FASEB J. Jan. 2013;27(1):25-33.
Varlamov, et al., Sex-specific differences in lipid and glucose metabolism. Front Endocrinol (Lausanne). Jan. 19, 2015;5:241.
Wei, et al., Targeted deletion of C1q/TNF-related protein 9 increases food intake, decreases insulin sensitivity, and promotes hepatic steatosis in mice. Am J Physiol Endocrinol Metab. Apr. 1, 2014;306(7):E779-90.
Wei, et al., C1q/TNF-related protein-12 (CTRP12), a novel adipokine that improves insulin sensitivity and glycemic control in mouse models of obesity and diabetes. J Biol Chem. Mar. 23, 2012;287(13):10301-15.
Wei, et al., Metabolic regulation by C1q/TNF-related protein-13 (CTRP13): activation OF AMP-activated protein kinase and suppression of fatty acid-induced JNK signaling. J Biol Chem. May 6, 2011;286(18):15652-65.
Wei, et al., C1q/Tumor Necrosis Factor-related Protein 11 (CTRP11), a Novel Adipose Stroma-derived Regulator of Adipogeness. J Biol Chem. Apr. 12, 2013;288(15):10214-29.
Weisberg, et al., Obesity is associated with macrophage accumulation in adipose tissue. J Clin Invest. Dec. 2003;112(12):1796-808.
Wolf, et al., CTRP3 deficiency reduces liver size and alters IL-6 and TGF-beta levels in obese mice. Am J Physiol Endocrinol Metab. Mar. 1, 2016;310(5):E332-45.
Wong, et al., Identification and characterization of CTRP9, a novel secreted glycoprotein, from adipose tissue that reduces serum glucose in mice and forms heterotrimers with adiponectin. FASEB J. Jan. 2009;23(1):241-58.
Wong, et al., Molecular, biochemical and functional characterizations of C1q/TNF family members: adipose-tissue-selective expression patterns, regulation by PPAR-gamma agonist, cysteine-mediated oligomerizations, combinatorial associations and metabolic functions. Biochem J. Dec. 1, 2008;416(2):161-77.
Wong, et al., A family of Acrp30/adiponectin structural and functional paralogs. Proc Natl Acad Sci U S A. Jul. 13, 2004;101(28):10302-7.
Wu, et al., CTRP3 attenuates post-infarct cardiac fibrosis by targeting Smad3 activation and inhibiting myofibroblast differentiation. J Mol Med (Berl). Dec. 2015;93(12):1311-25.
Xin, et al., Elevated circulating levels of CTRP1, a novel adipokine, in diabetic patients. Endocr J. 2014,61(9):841-7.
Xu, et al., Chronic inflammation in fat plays a crucial role in the development of obesity-related insulin resistance. J Clin Invest. Dec. 2003;112(12):1821-30.
Ye, et al., Adiponectin, driver or passenger on the road to insulin sensitivity? Mol Metab. Apr. 19, 2013;2(3):133-41.
Yen, et al., Thematic review series: glycerolipids. DGAT enzymes and triacylglycerol biosynthesis. J Lipid Res. Nov. 2008;49(11):2283-301.
Yi, et al., C1q/tumor necrosis factor-related protein-3, a newly identified adipokine, is a novel antiapoptotic, proangiogenic, and cardioprotective molecule in the ischemic mouse heart. Circulation. Jun. 26, 2012;125(25):3159-69.
Yuasa, et al., C1q/TNF-related protein-1 functions to protect against acute ischemic injury in the heart. FASEB J. Mar. 2016;30(3):1065-75.
Yuasa, et al., Association of circulating C1q/TNF-related protein 1 levels with coronary artery disease in men. PLoS One. Jun. 19, 2014;9(6):e99846.
Zheng, et al., C1q/TNF-Related Proteins, A Family of Novel Adipokines, Induce Vascular Relaxation Through the Adiponectin Receptor-1/AMPK/eNOS/Nitric Oxide Signaling Pathway. Arterioscler Thromb Vase Biol. Nov. 2011;31(11):2616-23.
Trujillo, et al., Adipose tissue-derived factors: impact on health and disease. Endocr Rev. Dec. 2006;27(7):762-78.

Ahima, et al., Brain adipocytokine action and metabolic regulation. Diabetes. Dec. 2006;55 Suppl 2:S145-54.
Scherer, et al., A novel serum protein similar to C1q, produced exclusively in adipocytes. J Biol Chem. Nov. 10, 1995;270(45):26746-9.
Hu, et al., AdipoQ is a novel adipose-specific gene dysregulated in obesity. J Biol Chem. May 3, 1996;271(18):10697-703.
Maeda, et al., cDNA cloning and expression of a novel adipose specific collagen-like factor, apM1 (AdiPose Most abundant Gene transcript 1). Biochem Biophys Res Commun. Apr. 16, 1996;221(2):286-9.
Ruan, et al., Tumor necrosis factor-α suppresses adipocyte-specific genes and activates expression of preadipocyte genes in 3T3-L1 adipocytes: nuclear factor-κB activation by TNF-α is obligatory. Diabetes. May 2002;51(5):1319-36.
Vasseur, et al., Hypoadiponectinaemia and high risk of type 2 diabetes are associated with adiponectin-encoding (ACDC) gene promoter variants in morbid obesity: evidence for a role of ACDC in diabesity. Diabetologia. May 2005,48(5):892-9.
Maeda, et al., PPARγ ligands increase expression and plasma concentrations of adiponectin, an adipose-derived protein. Diabetes. Sep. 2001;50(9):2094-9.
Esposito, et al., Effect of weight loss and lifestyle changes on vascular inflammatory markers in obese women: a randomized trial. JAMA. Apr. 9, 2003;289(14):1799-804.
Fruebis, et al., Proteolytic cleavage product of 30-κDa adipocyte complement-related protein increases fatty acid oxidation in muscle and causes weight loss in mice. Proc Natl Acad Sci U S A. Feb. 13, 2001;98(4):2005-10.
Yamauchi, et al., The fat-derived hormone adiponectin reverses insulin resistance associated with both lipoatrophy and obesity. Nat Med. Aug. 2001;7(8):941-6.
Berg, et al., The adipocyte-secreted protein Acrp30 enhances hepatic insulin action. Nat Med. Aug. 2001;7(8):947-53.
Shapiro, et al., The crystal structure of a complement-1q family protein suggests an evolutionary link to tumor necrosis factor. Curr Biol. Mar. 12, 1998;8(6):335-8.
Kishore, et al., C1q and tumor necrosis factor superfamily: modularity and versatility. Trends Immunol. Oct. 2004;25(10):551-61.
Lasser, et al., C1qTNF-related protein-1 (CTRP-1): a vascular wall protein that inhibits collagen-induced platelet aggregation by blocking VWF binding to collagen. Blood. Jan. 15, 2006;107(2):423-30.
Akiyama, et al., Cartducin stimulates mesenchymal chondroprogenitor cell proliferation through both extracellular signal-regulated kinase and phosphatidylinositol 3-kinase/Akt pathways. FEBS J. May 2006;273(10):2257-63.
Hayward, et al., Mutation in a short-chain collagen gene, CTRP5, results in extracellular deposit formation in late-onset retinal degeneration: a genetic model for age-related macular degeneration. Hum Mol Genet. Oct. 15, 2003;12(20):2657-67.
Chang, et al., Phenotype-based identification of host genes required for replication of African swine fever virus. J Virol. Sep. 2006;80(17):8705-17.
Zhang, et al., Bcr-Abl efficiently induces a myeloproliferative disease and production of excess interleukin-3 and granulocyte-macrophage colony-stimulating factor in mice: a novel model for chronic myelogenous leukemia. Blood. Nov. 15, 1998;92(10):3829-40.
Liu, et al., Generation of mammalian cells stably expressing multiple genes at predetermined levels. Anal Biochem. Apr. 10, 2000;280(1):20-8.
West, et al., Dietary obesity in nine inbred mouse strains. Am J Physiol. Jun. 1992;262(6 Pt 2):R1025-32.
Haluzik, et al., Genetic background (C57BL/6J versus FVB/N) strongly influences the severity of diabetes and insulin resistance in ob /ob mice. Endocrinology. Jul. 2004;145(7):3258-64.
Tsao, et al., Oligomerization state-dependent activation of NF-κB signaling pathway by adipocyte complement-related protein of 30 κDa (Acrp30). J Biol Chem. Aug. 16, 2002;277(33):29359-62.
Pajvani, et al., Structure—function studies of the adipocyte-secreted hormone Acrp30/adiponectin. Implications for metabolic regulation and bioactivity. J Biol Chem. Mar. 14, 2003;278(11):9073-85.

(56) References Cited

OTHER PUBLICATIONS

Suzuki, et al., The oligomeric structure of high molecular weight adiponectin. FEBS Lett. Mar. 6, 2007;581(5):809-814.

Tsao, et al., Role of disulfide bonds in Acrp30/adiponectin structure and signaling specificity. Different oligomers activate different signal transduction pathways. J Biol Chem. Dec. 12, 2003;278(50):50810-7.

Kishore, et al., C1q: structure, function, and receptors. Immunophamnacology. Aug. 2000;49(1-2):159-70.

Bao, et al., Cbln1 is essential for interaction-dependent secretion of Cbln3. Mol Cell Biol. Dec. 2006;26(24):9327-37.

Kondo, et al., Identification of novel blood proteins specific for mammalian hibernation. J Biol Chem. Jan. 5, 1992;267(1):473-8.

Mitchell, et al., Immunophenotype of human adipose-derived cells: temporal changes in stromal-associated and stem cell-associated markers. Stem Cells. Feb. 2006;24(2):376-85.

Schaffler, et al., Genomic organization, chromosomal localization and adipocytic expression of the murine gene for CORS-26 (collagenous repeat-containing sequence of 26 κDa protein). Biochim Biophys Acta. Jul. 9, 2003;1628(1):64-70.

CINTI, Anatomy of the adipose organ. Eat Weight Disord. Sep. 2000;5(3):132-42.

Rangwala, et al., Peroxisome proliferator-activated receptor γ in diabetes and metabolism. Trends Pharmacol Sci. Jun. 2004;25(6):331-6.

Peterson, J., et al., "CTRP1 Protein Enhances Fatty Acid Oxidation via AMP-activated Protein Kinase (AMPK) Activation and Acetyl-CoA Carboxylase (ACC) Inhibition" The Journal of Biological Chemistry vol. 287, No. 2, pp. 1576-1587, Jan. 6, 2012.

Wolf, R., et al., "CTRP3 deficiency reduces liver size and alters IL-6 and TGF levels in obese mice" Am J Physiol Endocrinol Metab 310: E332-E345, 2016.

Wong, G., et al., "A family of Acrp30 diponectin structural and functional paralogs" PNAS, Jul. 13, 2004, vol. 101, No. 28, pp. 10302-10307.

Wong, G., et al., "Molecular, biochemical and functional characterizations of C1q/TNF family members: adipose-tissue-selective expression patterns, regulation by PPAR-y agonist, cysteine-mediated oligomerizations, combinatorial associations and metabolic functions" Biochem J. Dec. 1, 2008; 416(2): 161-177. doi:10.1042/BJ20081240.

Arita et al., "Paradoxical Decrease of an Adipose-Specific Protein, Adiponectin, in Obesity." Biochemical and Biophysical Research Communications, 1999, pp. 79-83, vol. 257, Academic Press.

\* cited by examiner

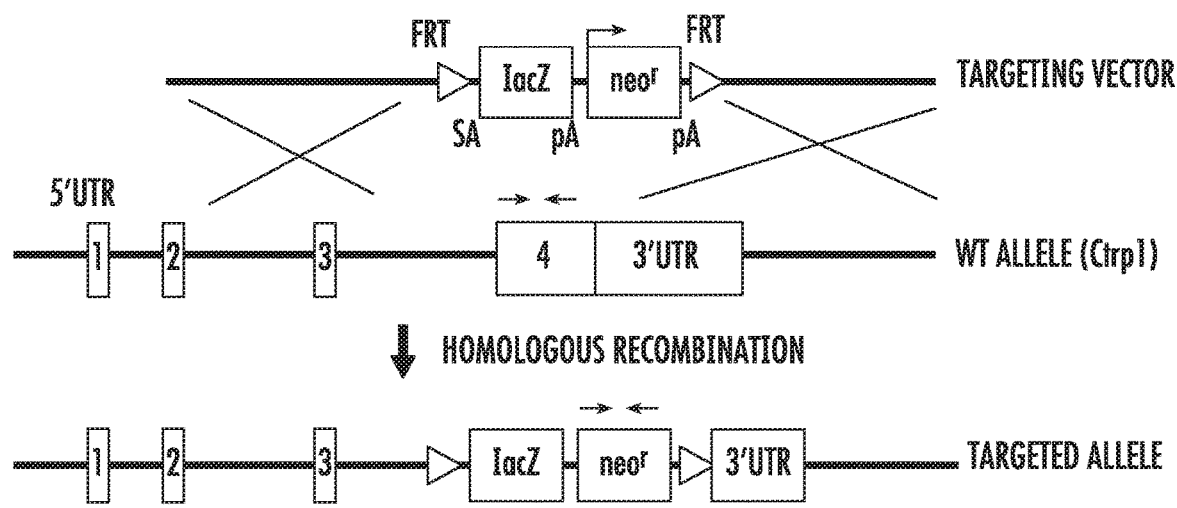
FIG. 1A
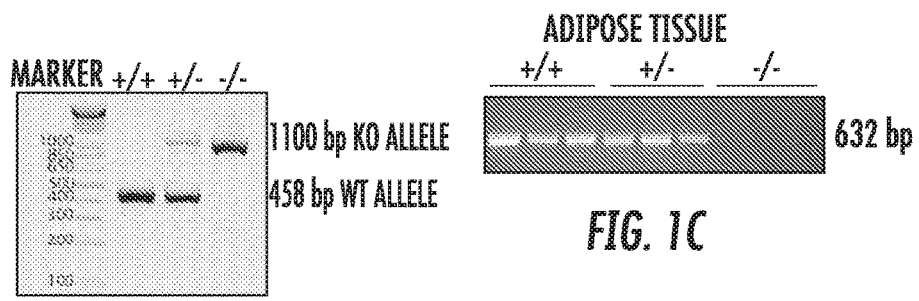
FIG. 1B
FIG. 1C
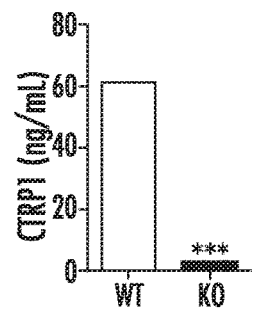
FIG. 1D

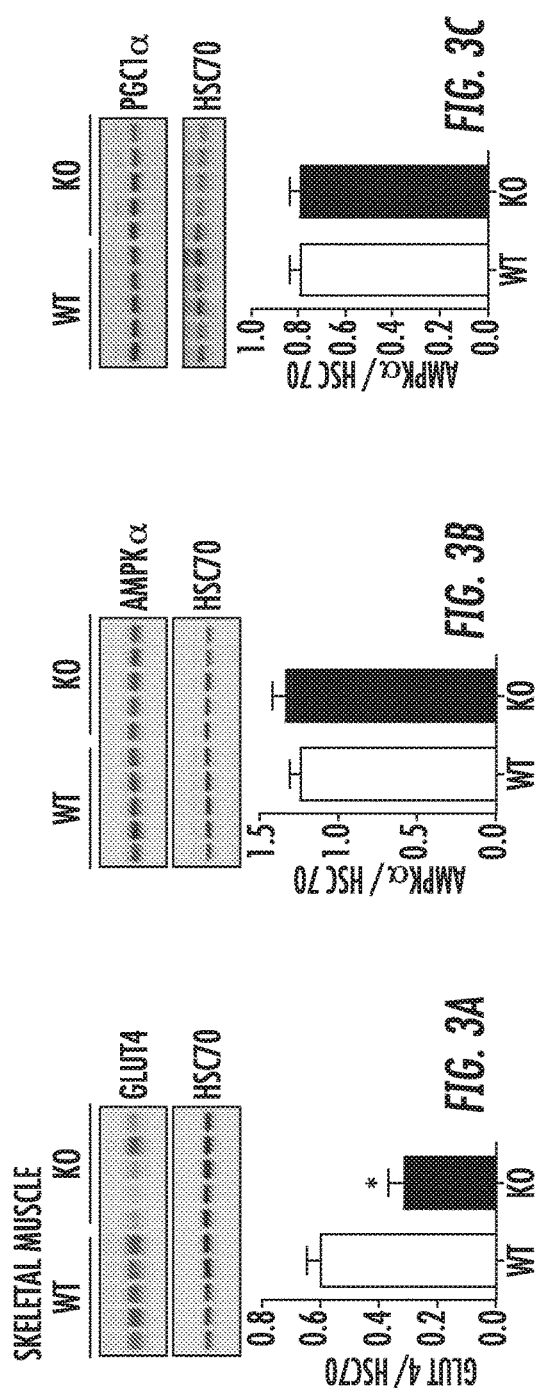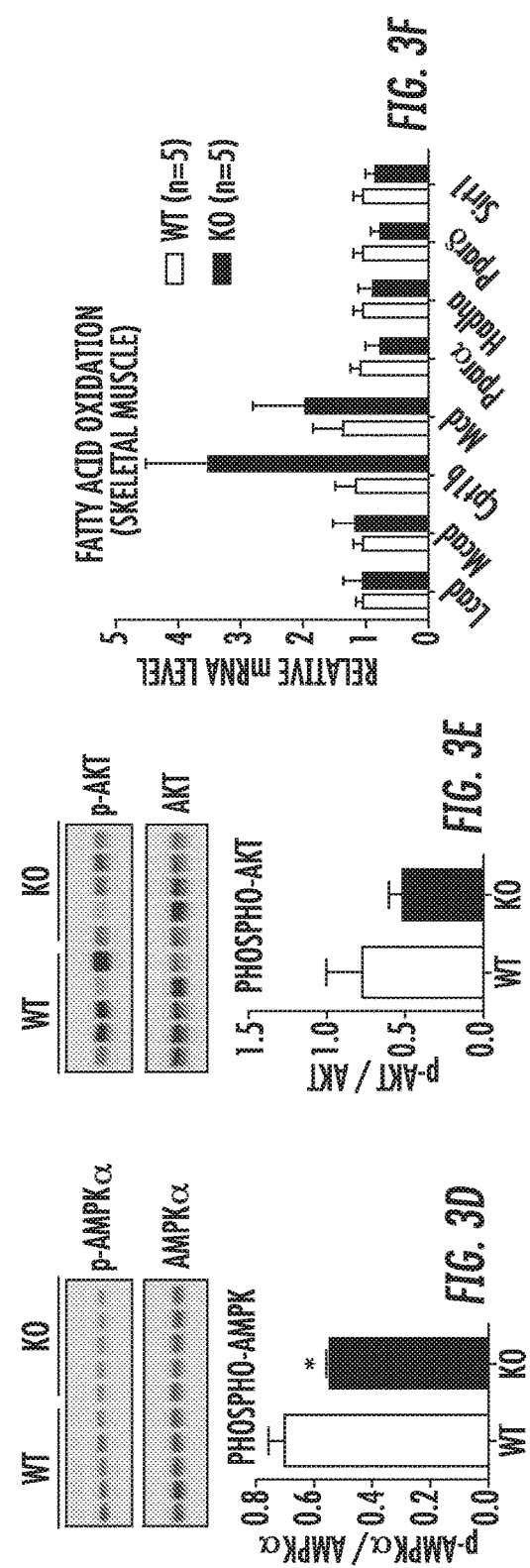

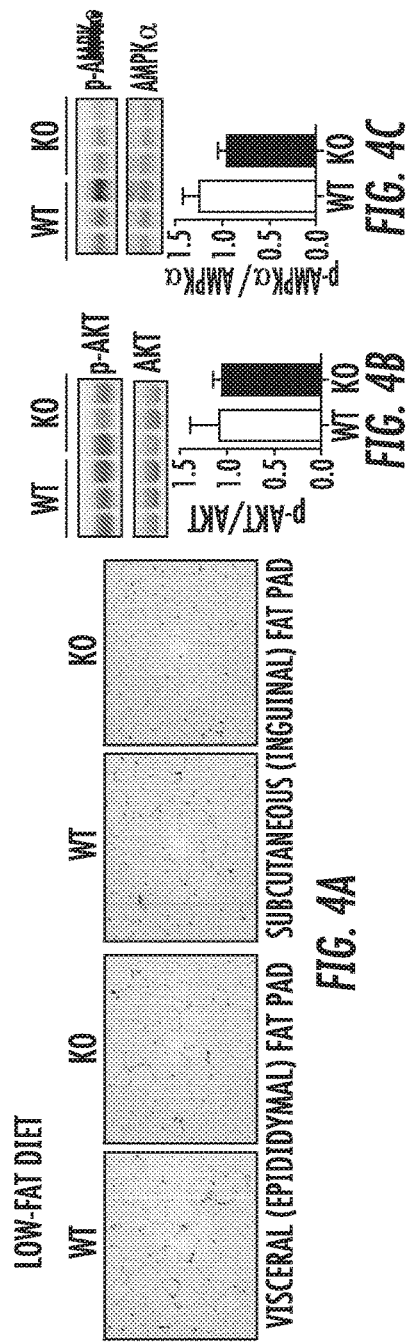
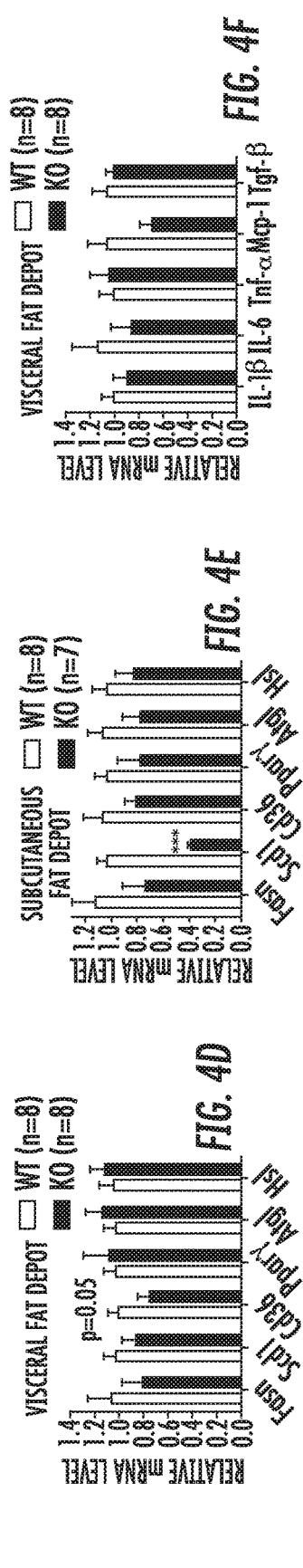

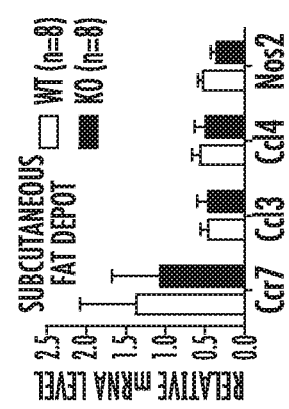
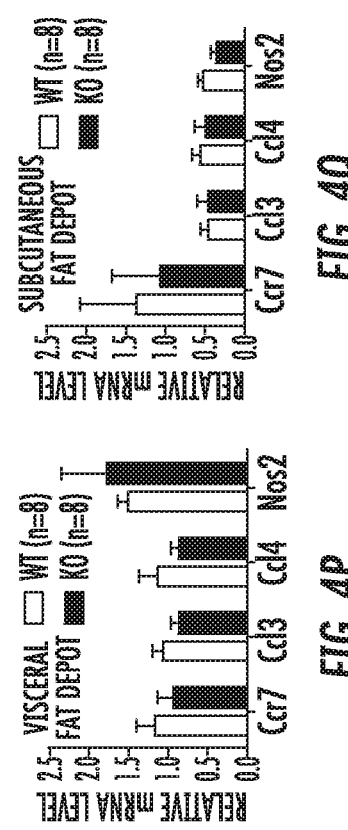
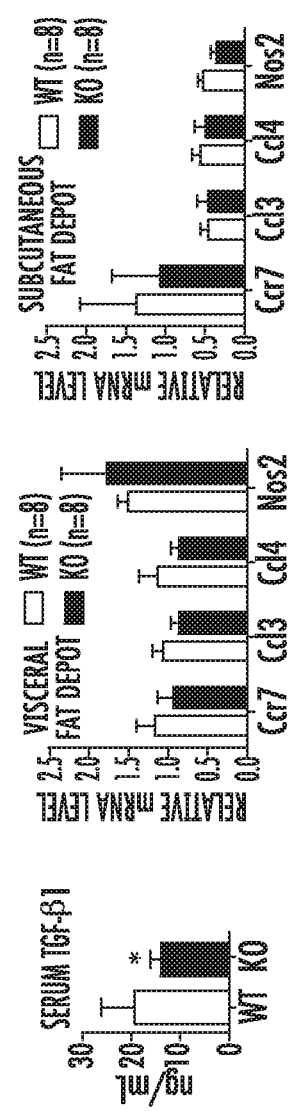
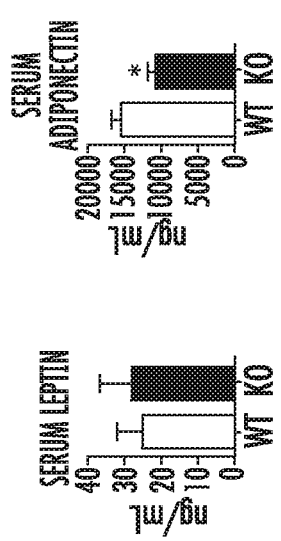
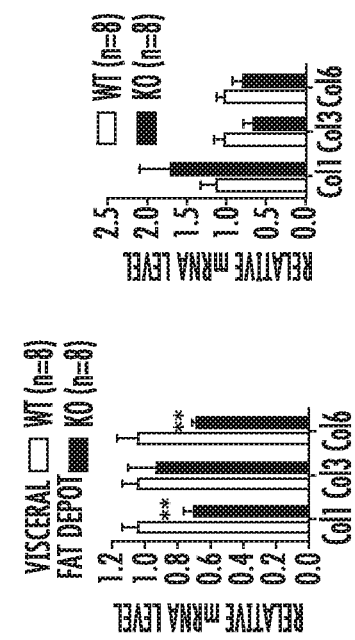
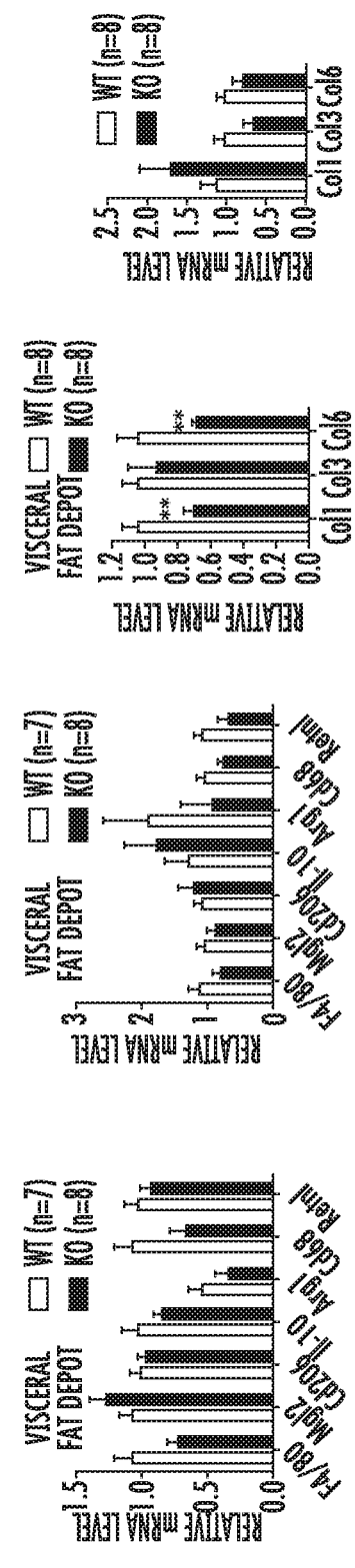

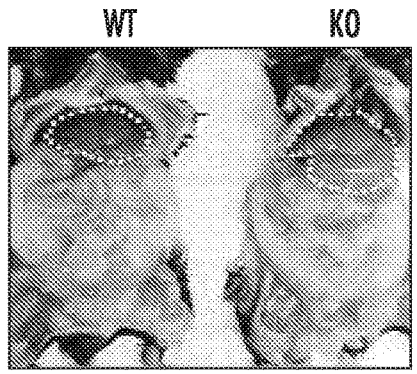
FIG. 5A
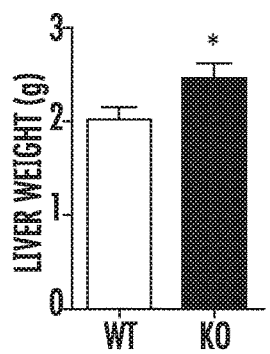
FIG. 5B
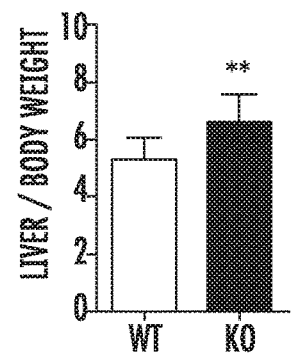
FIG. 5C
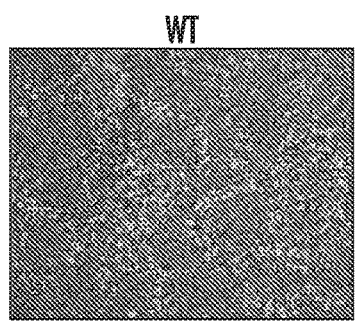
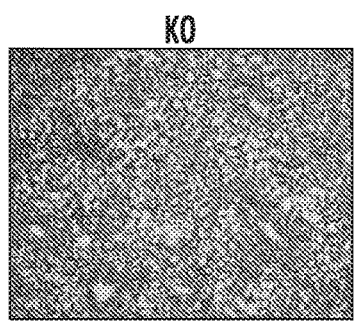
FIG. 5D
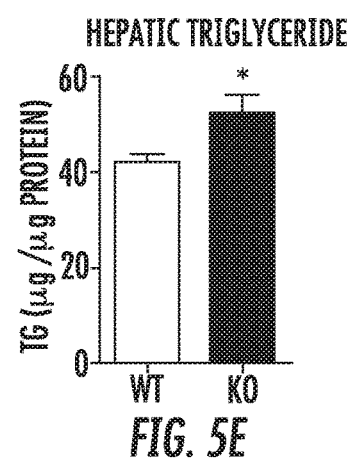
FIG. 5E
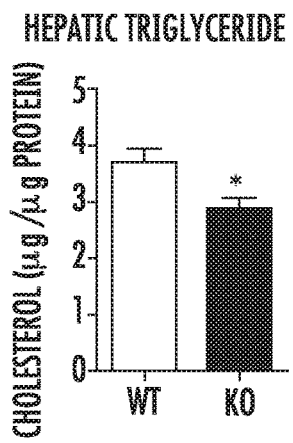
FIG. 5F
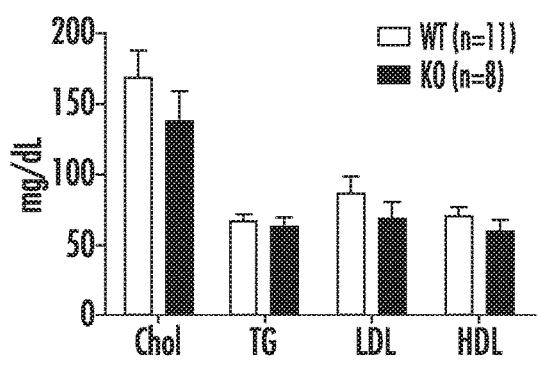
FIG. 5G
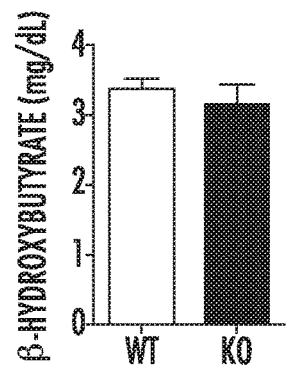
FIG. 5H

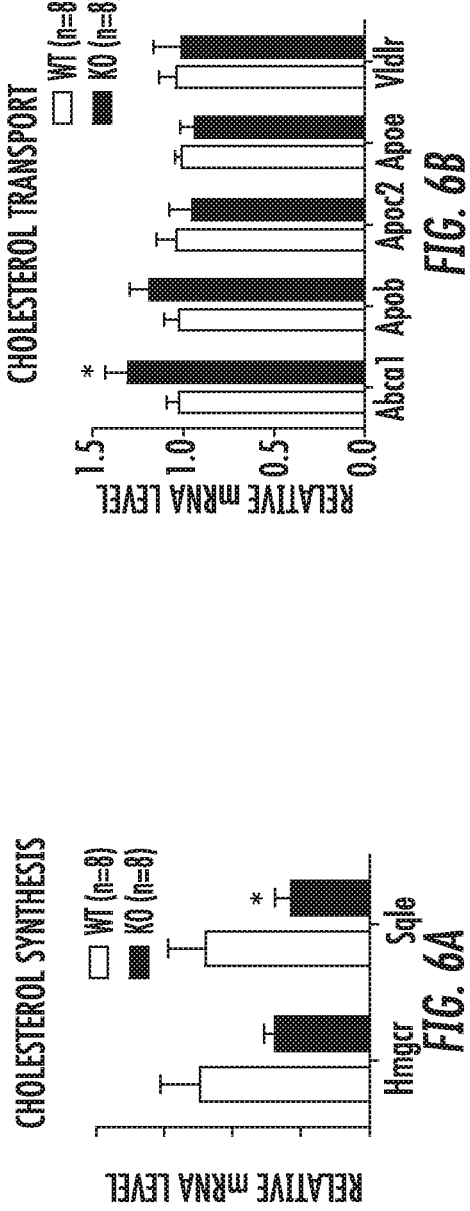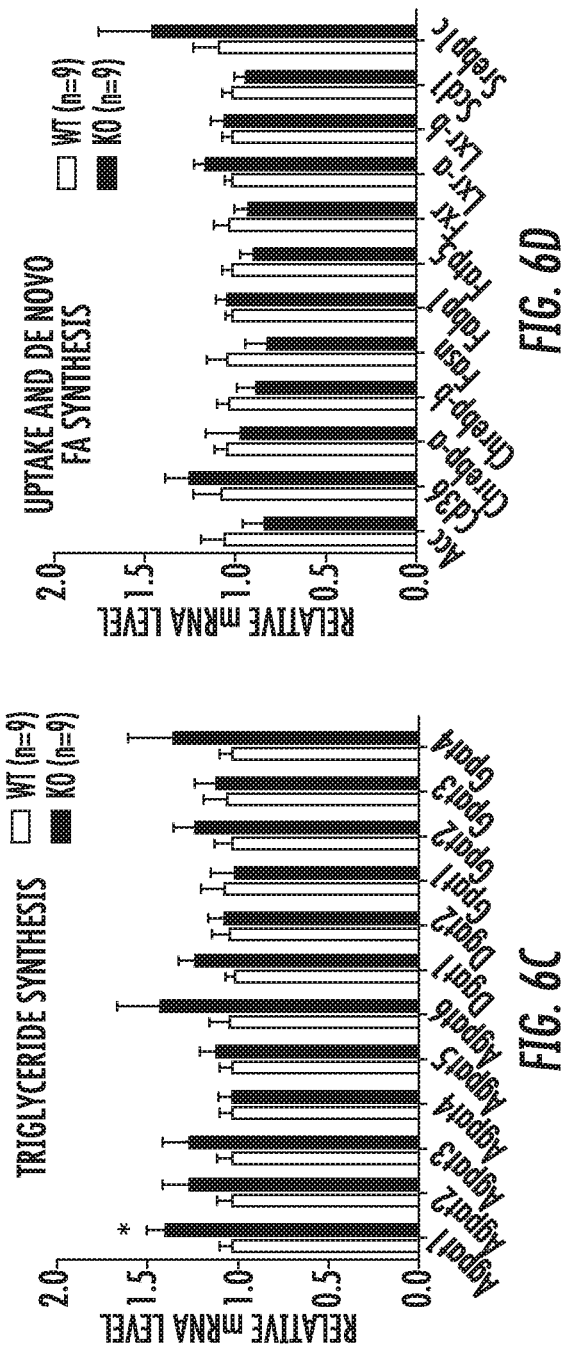
FIG. 6A  FIG. 6B  FIG. 6C  FIG. 6D

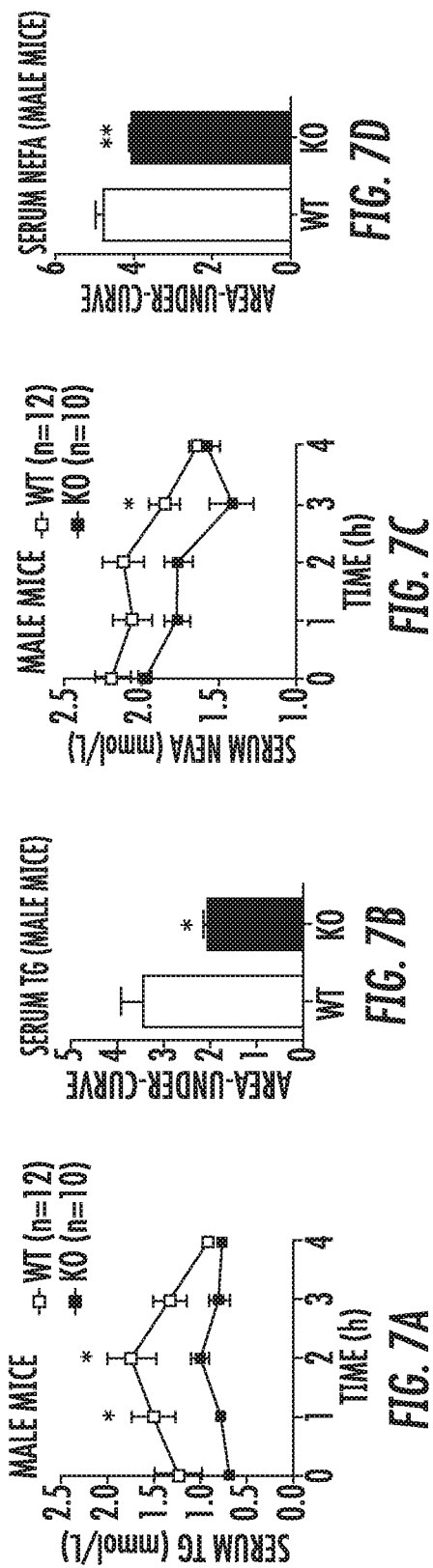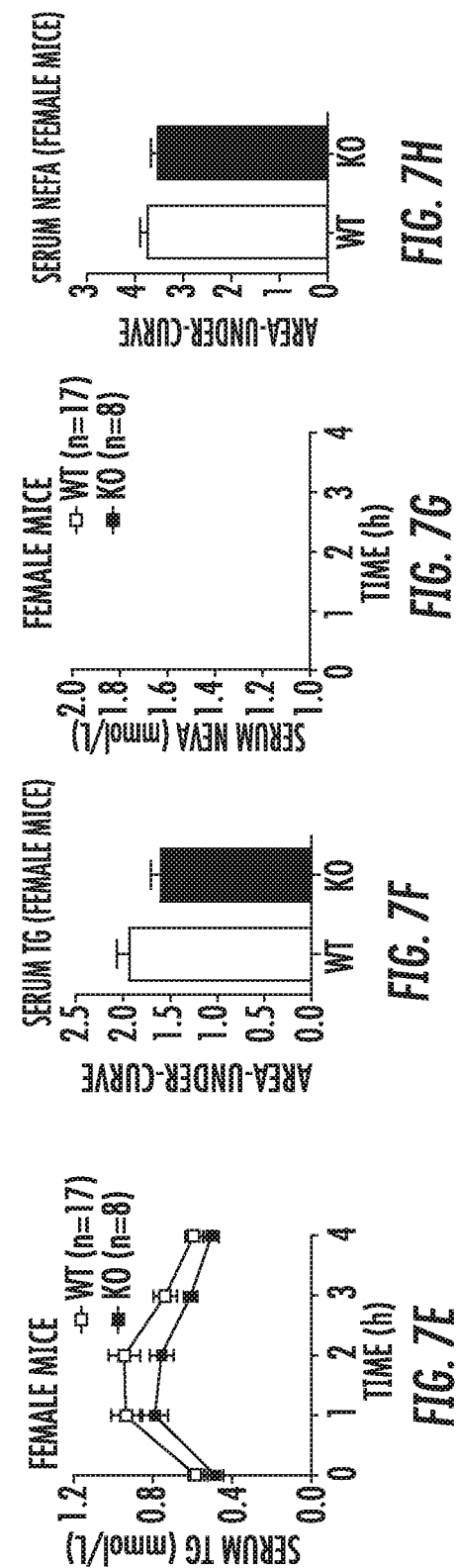

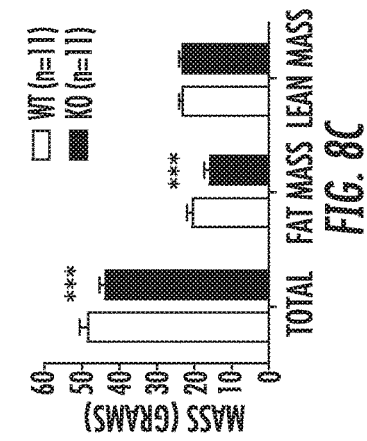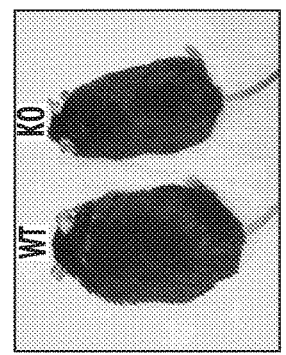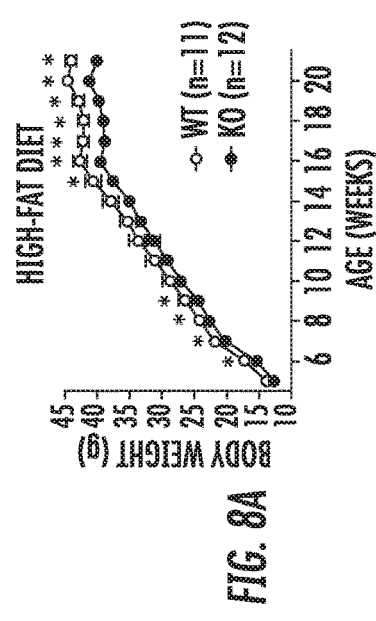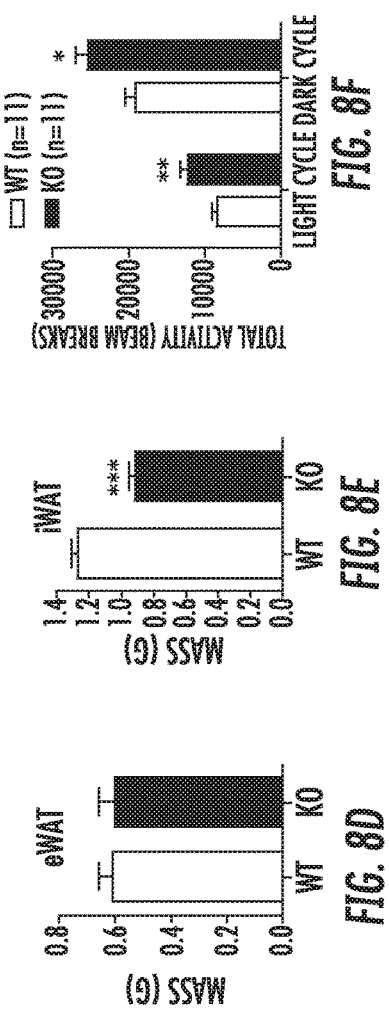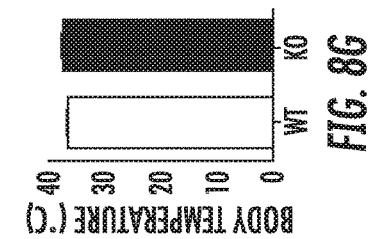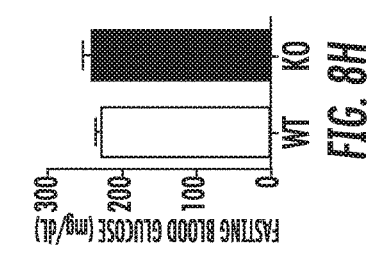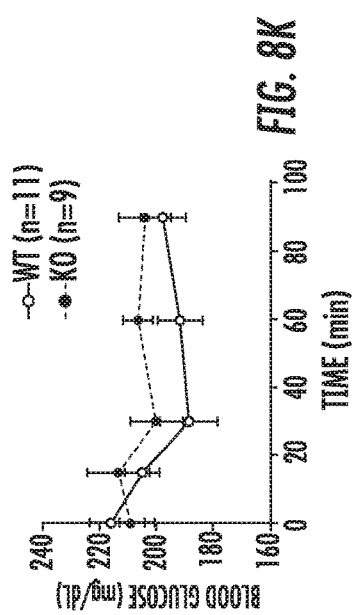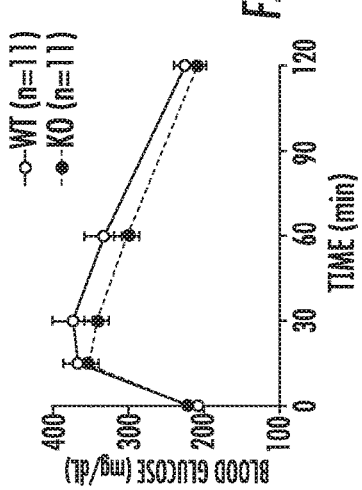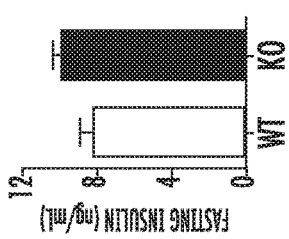

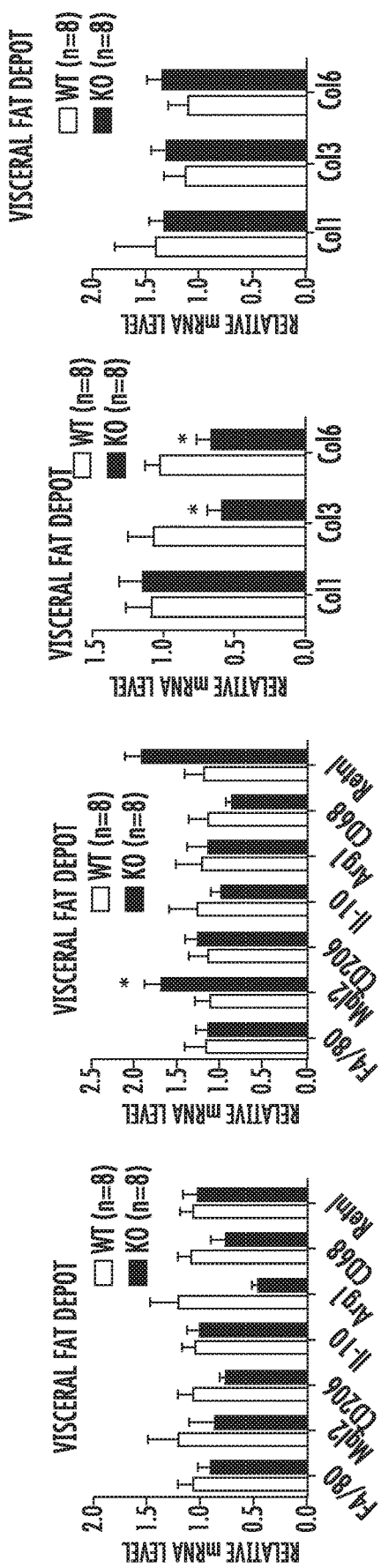
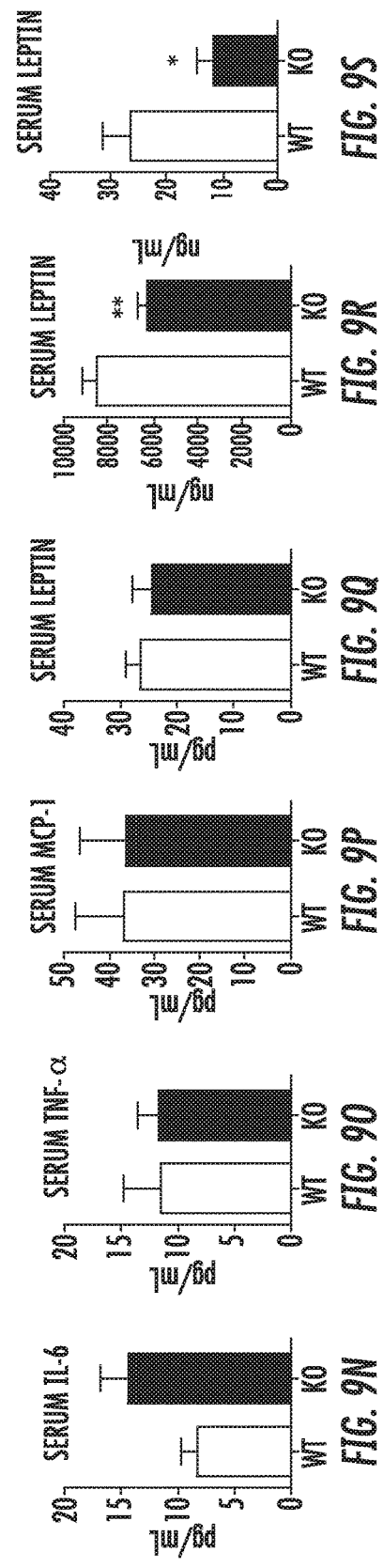

CTRP1-KO MICE (ON LOW-FAT DIET; COHORT 6) OVERNIGHT FAST  
AGE: 52 WEEKS (ON LOW-FAT DIET FOR 47 WEEKS)

WT n=5  
KO n=6

CTRP1 KO HFD MALES: COHORT 2 OVERNIGHT FAST
AGE: 62 WEEKS   WT=8
HFD: 56 WEEKS   KO=17

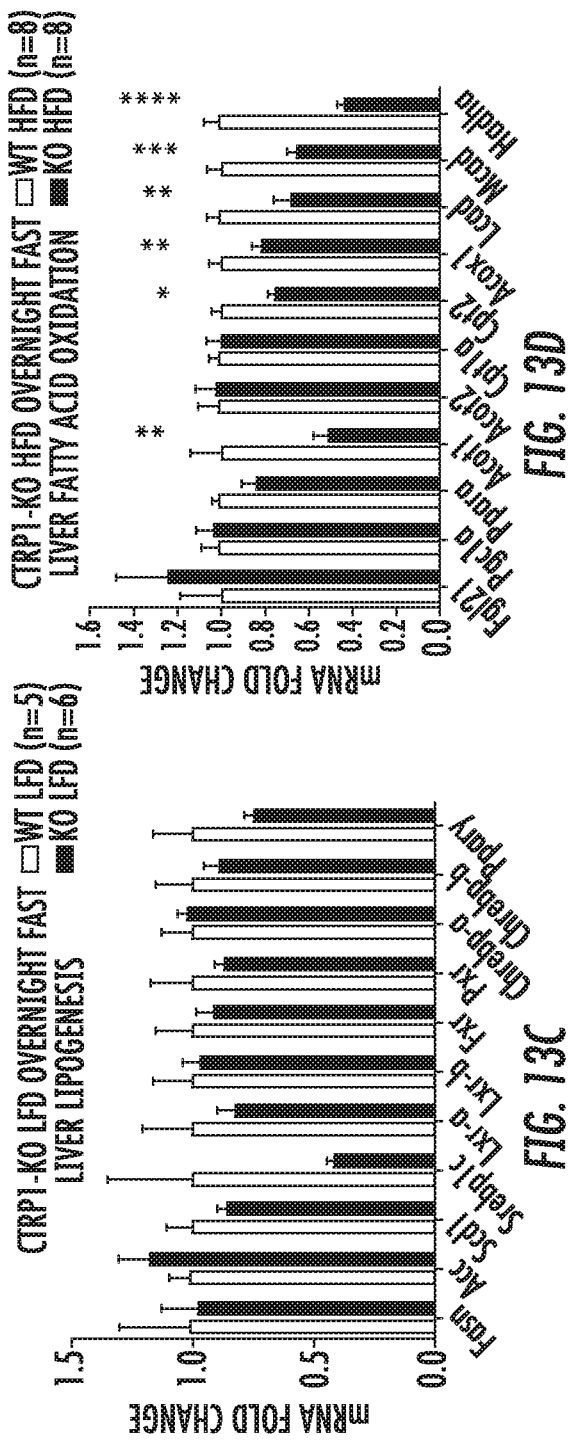
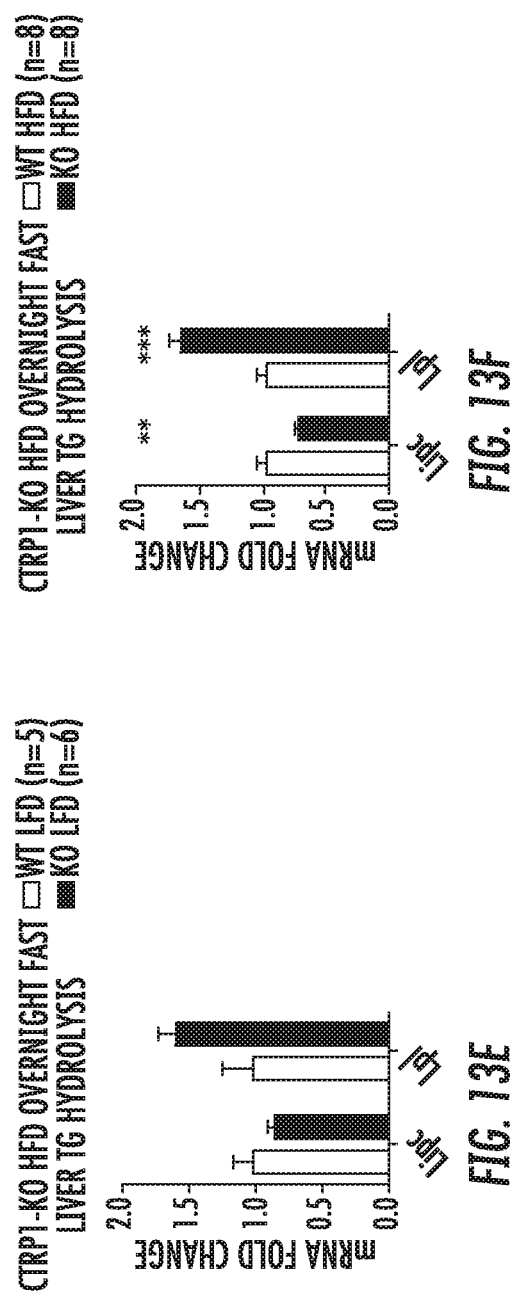

SEQUENCE LISTING

<160> NUMBER OF SEQ ID NOS: 77

<210> SEQ ID NO 1
<211> LENGTH: 281
<212> TYPE: PRT
<213> ORGANISM: Homo sapiens

<400> SEQUENCE: 1

Met Gly Ser Arg Gly Gln Gly Leu Leu Ala Tyr Cys Leu Leu Leu
1               5                   10                  15

Ala Phe Ala Ser Gly Leu Val Leu Ser Arg Val Pro His Val Gln Gly
            20                  25                  30

Glu Gln Gln Glu Trp Glu Gly Thr Glu Leu Pro Ser Pro Pro Asp
        35                  40                  45

His Ala Glu Arg Ala Glu Glu Gln His Glu Lys Tyr Arg Pro Ser Gln
    50                  55                  60

Asp Gln Gly Leu Pro Ala Ser Arg Cys Leu Arg Cys Cys Asp Pro Gly
65                  70                  75                  80

Thr Ser Met Tyr Pro Ala Thr Ala Val Pro Gln Ile Asn Ile Thr Ile
                85                  90                  95

Leu Lys Gly Glu Lys Gly Asp Arg Gly Asp Arg Gly Leu Gln Gly Lys
            100                 105                 110

Tyr Gly Lys Thr Gly Ser Ala Gly Ala Arg Gly His Thr Gly Pro Lys
        115                 120                 125

Gly Gln Lys Gly Ser Met Gly Ala Pro Gly Glu Arg Cys Lys Ser His
    130                 135                 140

Tyr Ala Ala Phe Ser Val Gly Arg Lys Lys Pro Met His Ser Asn His
145                 150                 155                 160

Tyr Tyr Gln Thr Val Ile Phe Asp Thr Glu Phe Val Asn Leu Tyr Asp
                165                 170                 175

His Phe Asn Met Phe Thr Gly Lys Phe Tyr Cys Tyr Val Pro Gly Leu
            180                 185                 190

Tyr Phe Phe Ser Leu Asn Val His Thr Trp Asn Gln Lys Glu Thr Tyr
        195                 200                 205

Leu His Ile Met Lys Asn Glu Glu Glu Val Val Ile Leu Phe Ala Gln
    210                 215                 220

Val Gly Asp Arg Ser Ile Met Gln Ser Gln Ser Leu Met Leu Glu Leu
225                 230                 235                 240

Arg Glu Gln Asp Gln Val Trp Val Arg Leu Tyr Lys Gly Glu Arg Glu
                245                 250                 255

Asn Ala Ile Phe Ser Glu Glu Leu Asp Thr Tyr Ile Thr Phe Ser Gly
            260                 265                 270

Tyr Leu Val Lys His Ala Thr Glu Pro
        275                 280

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggttctacag gtcccaggg                                               19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtgatgtagg tgtcgaactc g                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcagcgcatc gccttctatc g                                            21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggaagtccct ctcacgtgtc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgaggacct ccccacttct                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaccaggtag ccactgaagg                                              20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agattcggga tatgctgttg gc                                                    22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcgggtccta gaccagtgtt c                                                     21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttgtggaat gccttgtgat tg                                                    22

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agccgaagca gcacatgat                                                        19

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ataagaaatg cggggatgtc ac                                                    22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atatccgaga aggcagcgaa c                                                     21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctgcaggaa tccagagaat                                                       20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
catgcacaag gtcctgagaa                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aggttccggc ttgatgagaa                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agtgggttgg caggctttat                                              20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctgacaggat gcctagccg                                               19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgcaggtaat cccagaagc                                               19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gagcccctga aggaatgcc                                               19

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctataacta ggtctttgca gatatgg                                        27

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atgggctgtg atcggaactg                                                20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agccaggact gcaccaataa c                                              21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgacactcac ccacctcttc                                                20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttgttcagcc ggatcttgtc                                                20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agcggattcc aggtgagg                                                  18

```
<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttgttcaggc ggatcttgtc                                                 20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atgaacttct ccggcaagta cc                                              22

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggtcctcggg cagacctat                                                  19

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gttctcccgt ccaagaccat t                                               21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gctccgtaca gagtgtagca ag                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcttgatgtg ctacaaaagc tg                                              22

<210> SEQ ID NO 33
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgtggtgatg gttgaatgtc c                                             21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aggagtgtcg acttccgcaa a                                             21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctcttcttgc cgcttcagtt t                                             21

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atagtgggtc acgaagcagc                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agggcaacag agtcggagac                                               20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cccagtcgta cacgtcattt t                                             21

<210> SEQ ID NO 39
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
catcattctc atggtcctgc t                                               21

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctcgggacct tcctcataaa gaga                                            24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaatagttcg ttcctcccat gctc                                            24

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atgggaaatc ccctccaaat ct                                              22

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtgctgaggt ctgagacga                                                  19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccctgaagac acagctgagg                                                 20

<210> SEQ ID NO 45
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 45
ggctgtaccc taagaggtgg                                                  20

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ttaaaaacct ggatcggaac caa                                              23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcattagctt cagatttacg ggt                                              23

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccagagtctg ctgatctgcg                                                  20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gccacctctt tgctctgctc                                                  20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgtggcctca ttcctcctac                                                  20

<210> SEQ ID NO 51
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 51
tcgtggatgt tggtggagct                                                   20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctgggctgt caagcactgt                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtaactgggt aggctgccat                                                   20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgtacgagtc ggtgtgcttc                                                   20

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggtaggtatc cgtcatggtc ttg                                               23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttctctgtac catgacactc tgc                                               23

<210> SEQ ID NO 57
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 57
cgtggaatct tccggctgta g                                              21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttcctgctgt ttctcttaca cct                                            23

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctgtctgcct cttttggtca g                                              21

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gttctcagcc caacaataca aga                                            23

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtggacgggt cgatgtcac                                                 19

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccccagtgtc cttacagagt g                                              21

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 63
gtgcccagag tggatgtct                                                19

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcatgaaggc agctgctatt ggtt                                          24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
taggcccatc cagctaagca catt                                          24

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ctctgttcag ctattggacg c                                             21

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cggaatttct gggattcagc ttc                                           23

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gctcttactg actggcatga g                                             21

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cgcagctcta ggagcatgtg                                                    20

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctccaagcca aagtccttag ag                                                 22

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aggagctgtc attagggaca tc                                                 22

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ttctgctgtg gaaatgcaag                                                    20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
caatgatgag aggcagcaag                                                    20

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccaatccagc taactatccc tcc                                                23

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 75
acccagtagc agtcatccca                                                    20

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gtgcccagag tggatgtct                                                     19

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccccgctttt gtcatattcc g                                                  21
```

USE OF C1Q/TNF-RELATED PROTEIN-1 (CTRP1) TO TREAT FATTY LIVER DISEASE

CROSS-REFERENCE TO RELATED APPLICATIONS

This application is a 35 U.S.C. § 371 U.S. national entry of International Application PCT/US2017/036535, having an international filing date of Jun. 8, 2017, which claims the benefit of U.S. Provisional Application No. 62/348,189, filed Jun. 10, 2016, the content of each of the aforementioned applications is herein incorporated by reference in their entirety.

REFERENCE TO RELATED APPLICATIONS

This application claims the benefit of U.S. Provisional Patent Application No. 62/348,189 filed on Jun. 10, 2016, which is hereby incorporated by reference for all purposes as if fully set forth herein.

STATEMENT OF GOVERNMENTAL INTEREST

This invention was made with government support under grant no. DK084171, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jun. 6, 2017, is named P14197-02_SL.txt and is 19,906 bytes in size.

BACKGROUND OF THE INVENTION

Fatty liver is the accumulation of triglycerides and other fats in the liver cells. The amount of fatty acid in the liver depends on the balance between the processes of delivery and removal. In some patients, fatty liver may be accompanied by hepatic inflammation and liver cell death (steatohepatitis). Potential pathophysiologic mechanisms for fatty liver include the following: decreased mitochondrial fatty acid beta-oxidation, increased endogenous fatty acid synthesis or enhanced delivery of fatty acids to the liver, and deficient incorporation or export of triglycerides as very low-density lipoprotein (VLDL). The mechanism involved in the formation of fatty liver must be identified to enable the creation of therapeutic agents able to prevent or treat disease.

SUMMARY OF THE INVENTION

One embodiment of the present invention is a method for the treatment or prevention of fatty liver disease in a subject comprising administering to the subject an effective amount of an agent that changes the amount of CTRP1 in a subject. When a subject is on a low fat diet it is preferred that the subject is given an agent that increases the amount of CTRP1 in the subject compared to the amount of CTRP1 in the subject before the agent is given. A suitable agent could be chemical, protein, peptide, antibody, CTRP1 or a functional part thereof as examples.

Another embodiment of the present invention is a method for the treatment or prevention of obesity in a subject comprising administering to the subject an effective amount of an agent that changes the amount of CTRP1 in the subject compared to the subject before the agent is given. When a subject is on a high fat diet it is preferred that the subject is given an agent that decreases the amount of CTRP1 in the subject compared to the amount of CTRP1 in the subject before the agent is given. Suitable agents may inhibit the expression or activity of CTRP1.

Another embodiment of the present invention is a mouse comprising a null allele for Ctrp1 comprising a deleted functional region of the Ctrp1 gene that spans exon 4 replaced with a reporter and a drug resistant cassette. A suitable functional region comprises a 679-bp of the Ctrp1 gene that spans exon 4, a suitable drug resistant cassette is a neomycin resistance cassette, and a suitable reporter is a lacZ reporter.

The term "activity" refers to the ability of a gene to perform its function such as ZnT8 (a zinc transporter) being able to transport zinc.

The term "CTRP1" refers to the C1q/TNF-Related Protein-1 and an example of a protein sequence of CTRP1 includes Accession number: NP_699203.1 GI: 388453007 (SEQ ID NO: 1):

```
  1 mgsrgqglll ayclllafas glvlsrvphv qgeqqewegt eelpsppdha eraeeqheky
 61 rpsqdqglpa srclrccdpg tsmypatavp qinitilkge kgdrgdrglq gkygktgsag
121 arghtgpkgq kgsmgapger ckshyaafsv grkkpmhsnh yyqtvifdte fvnlydhfnm
181 ftgkfycyvp glyffslnvh twnqketylh imkneeevvi lfaqvgdrsi mqsqslmlel
241 reqdqvwvrl ykgerenaif seeldtyitf sgylvkhate p
```

The term "express" refers to the ability of a gene to express the gene product including for example its corresponding mRNA or protein sequence (s).

The term "reference" refers to a standard or control conditions such as a sample (human cells for example) or subject free, or substantially free, of agent.

The term "reporter gene" or "reporter" refers to a gene that researchers attach to a regulatory sequence of another gene of interest in bacteria, cell culture, animals or plants. Certain genes are chosen as reporters because the characteristics they confer on organisms expressing them are easily identified and measured, or because they are selectable markers. Reporter genes are often used as an indication of whether a certain gene has been taken up by or expressed in the cell or organism population. Commonly used reporter genes that induce visually identifiable characteristics usually involve fluorescent and luminescent proteins. Examples include the gene that encodes jellyfish green fluorescent protein (GFP), which causes cells that express it to glow green under blue light, the enzyme luciferase, which catalyzes a reaction with luciferin to produce light, and the red fluorescent protein from the gene dsRed As used herein, the term "steatosis" also called "fatty change", "fatty degeneration", or "adipose degeneration" is the process describing the abnormal retention of lipids within a cell. It reflects an impairment of the normal processes of synthesis and elimination of triglyceride fat. Excess lipid accumulates in vesicles that displace the cytoplasm. When the vesicles are large enough to distort the nucleus, the condition is known as macrovesicular steatosis; otherwise, the condition is known as microvesicular steatosis. While not particularly detrimental to the cell in mild cases, large accumulations can disrupt cell constituents, and in severe cases the cell may even burst.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Glossary

ACC Acetyl CoA carboxylase
ACOX Acyl-coenzyme A oxidase
ACADM acyl-CoA dehydrogenase, C-4 to C-12 straight chain
ACADL Acyl-coenzyme A dehydrogenase, long chain
AdipoQ Adiponectin
AGPAT Acylglycerolphosphate acyltransferase
CPT2 carnitine palmitoyltransferase 2
CTRP C1q/TNF-related protein
DGAT Diacylglycerol acyltransferases
DIO Diet-induced obese
G6Pc Glucose 6-phosphatase
GPAT Glycerol-3-phosphate acyltransferase
GTT Glucose tolerance test
HDL High-density lipoprotein
HFD High-fat diet
HOMA-IR Homeostatic model assessment of insulin resistance
ITT Insulin tolerance test
IL-1β Interleukin 1β
IL-6 Interleukin-6
LDL Low-density lipoprotein
LEP Leptin
LFD Low-fat diet
MCP-1 Macrophage chemotactic protein 1
NEFA Non-esterified free fatty acid
NMR Nuclear magnetic resonance
PBS Phosphate buffered saline
RER Respiratory exchange ratio
RETN Resistin
RPLP0 Ribosomal phosphoprotein P0
TAG Triglyceride
TGF-β Transforming growth factor β
TNF-α Tumor necrosis factor-alpha
VLDL Very low-density lipoprotein
$VO_2$ Volume of oxygen consumption
$VCO_2$ Volume of carbon dioxide produced
WT Wild-type

BRIEF DESCRIPTION OF THE DRAWINGS

FIG. 1A-1D illustrates the generation of a Ctrp1 KO mouse model.

FIG. 3A-3F illustrates reduced expression of GLUT4 and AMPK in skeletal muscle of Ctrp1-KO male mice fed an LFD.

FIG. 4A-4U illustrates the impact of CTRP1 deficiency on the adipose tissue of LFD-fed male mice.

FIG. 5A-5H illustrates LFD-fed Ctrp1-KO male mice develop liver steatosis

FIG. 6A-6G illustrates quantitative real-time PCR analyses were performed to assess possible changes in the expression of hepatic lipid metabolism genes in LFD-fed-KO male mice.

FIG. 7A-7I illustrates enhanced lipid tolerance in LFD-fed Ctrp1-KO mice.

FIG. 8A-8K illustrates reduced body weight gain in CTRP1-KO mice fed a high-fat diet.

FIG. 13A-13F illustrates expression of fat oxidation genes in the liver were significantly down-regulated in overnight CTRP1 deficient animals and genes involved in lipid synthesis were up-regulated in CTRP1 KO mice.

DETAILED DESCRIPTION OF THE INVENTION

Figure 2A:
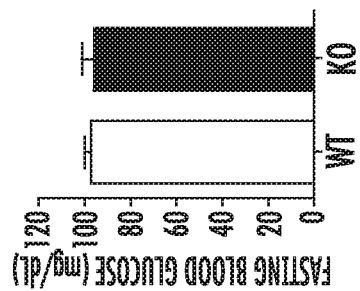
FIG. 2A-2H illustrates metabolic parameters of WT and Ctrp1-KO mice fed a low-fat diet.
Figure 2B:
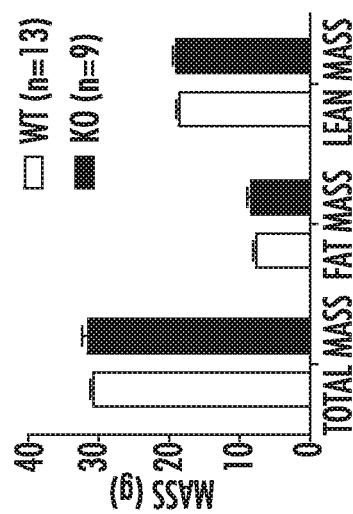
Figure 2C:
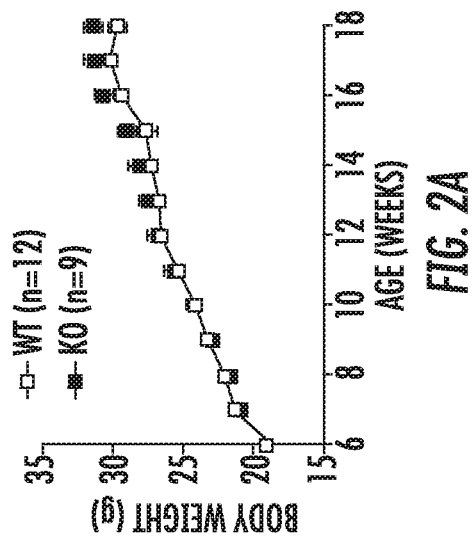
Figure 2D:
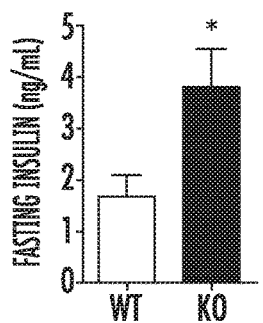
Figure 2E:
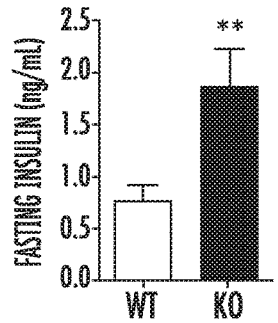
Figure 2F:
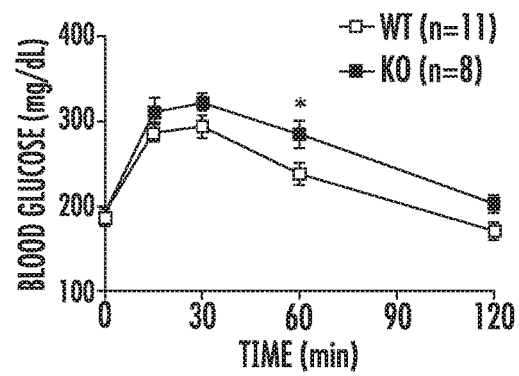
Figure 2G:
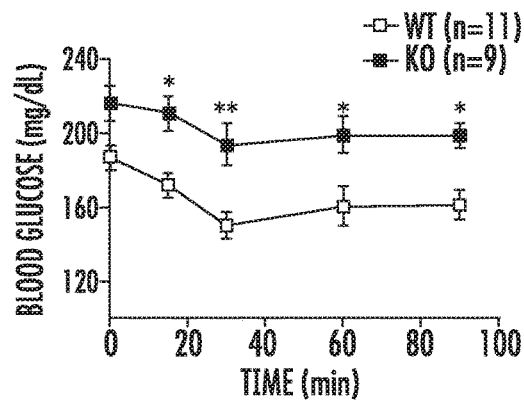
Figure 2H:
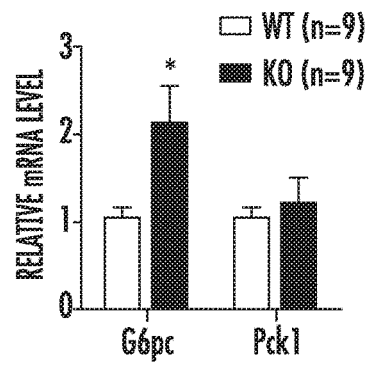

Secreted hormones control energy metabolism via inter-organ crosstalk, and their circulating levels are frequently dysregulated in the pathophysiological states of obesity and diabetes. In an effort to uncover novel metabolic regulators, we have characterized the C1q/TNF-related proteins (CTRP1-15), a highly conserved family of secreted proteins. Distinct and notable metabolic, cardiovascular, and inflammatory functions have been demonstrated for several members of this protein family based on in vivo functional studies. In vitro studies have also highlighted CTRP11's involvement in adipogenesis and CTRP13's role in antagonizing lipid-induced insulin resistance.

Similar to many CTRP family members, CTRP1 has a distinct expression profile, with the highest expression levels seen in adipose tissue. Adipose expression of CTRP1 and its circulating levels are modulated by the metabolic and inflammatory states of animals. Its expression is upregulated by the anti-diabetic drug, rosiglitazone, as well as in animals lacking the insulin-sensitizing hormone, adiponectin. Consistent with a metabolic role, administration of recombinant CTRP1 to wild-type mice acutely lowers blood glucose, and chronic overexpression of CTRP1 in transgenic mice enhances AMP-activated protein kinase (AMPK) activation and skeletal muscle fat oxidation, while attenuating insulin resistance induced by high-fat feeding.

The physiologic relevance of CTRP1 in the context of disease is highlighted by recent studies in humans with metabolic disorders. Circulating levels of CTRP1 are elevated in patients with type 2 diabetes and metabolic syndrome, as well as in patients with coronary artery disease and hypertension. Whether the observed upregulation of plasma CTRP1 seen in humans is a cause or a consequence of the disease remains to be established. In support of the notion that CTRP1 upregulation represents physiologic compensation, mice lacking CTRP1 protein have increased myocardial infarct size, cardiomyocyte apoptosis, and proinflammatory gene expression induced by ischemia/reperfusion injury, whereas systemic delivery of CTRP1 attenuated myocardial damage. In contrast, in an apolipoprotein E-deficient mouse model, CTRP1 appears to play an adverse role in promoting atherosclerosis and its deficiency attenuates disease severity. While earlier studies have demonstrated a positive metabolic role for CTRP1, the physiologic consequence of its deficiency on glucose and lipid metabolism has not been described. Given the significant caveats and limitations associated with previous recombinant protein infusion and transgenic overexpression studies, the present invention provides genetic evidence, using a knockout (KO) mouse model, that CTRP1 is indeed required for metabolic homeostasis and can be used as a therapeutic agent to treat or prevent disease such as liver steatosis (fatty liver).

Using a loss-of-function mouse model, the present invention provides critical genetic evidence that CTRP1 is required for metabolic homeostasis. Notably, though, the contributions of CTRP1 to energy metabolism depend on metabolic and dietary contexts. When mice are fed a low-fat diet, comparable to standard chow, loss of CTRP1 did not appear to affect body weight or metabolic rate ($VO_2$). Its deficiency, however, promoted insulin resistance independent of adiposity. Mice lacking CTRP1 exhibited elevated hepatic gluconeogenic gene expression, as well as elevated fasting insulin levels, and reduced rates of glucose disposal in response to glucose and insulin challenge compared to WT littermate controls (FIG. 2). In the absence of CTRP1, we also observed a reduction in the steady-state protein levels of AMPK and GLUT4 in the skeletal muscle relative to WT controls. Further, relative phosphorylated AMPKα (a metric of AMPK activation) was also reduced in the skeletal muscle of Ctrp1-KO animals (FIG. 3). Given that both AMPK and the glucose transporter GLUT4 are known to play important roles in skeletal muscle glucose uptake, the reduction in protein levels, along with decreased insulin action, likely contributes to reduced glucose disposal in response to glucose and insulin injection. In contrast to skeletal muscle, loss of CTRP1 did not alter steady-state AMPKα protein levels or relative phosphorylated AMPKα protein levels in adipose tissue (FIG. 4).

Figure 6G:
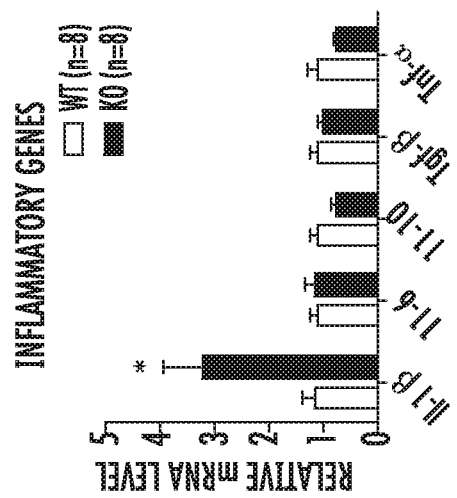
Figure 6F:
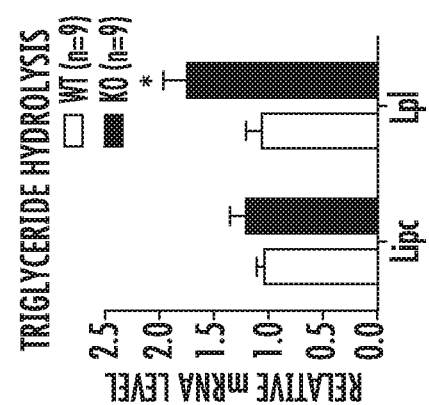
Figure 6E:
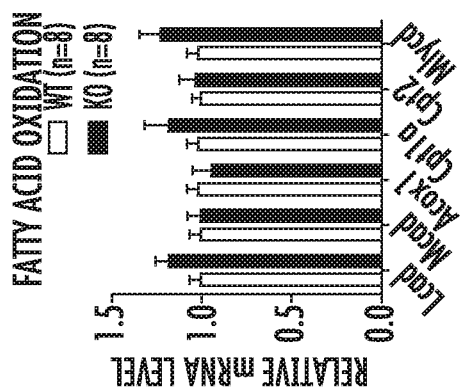
Figure 7I:
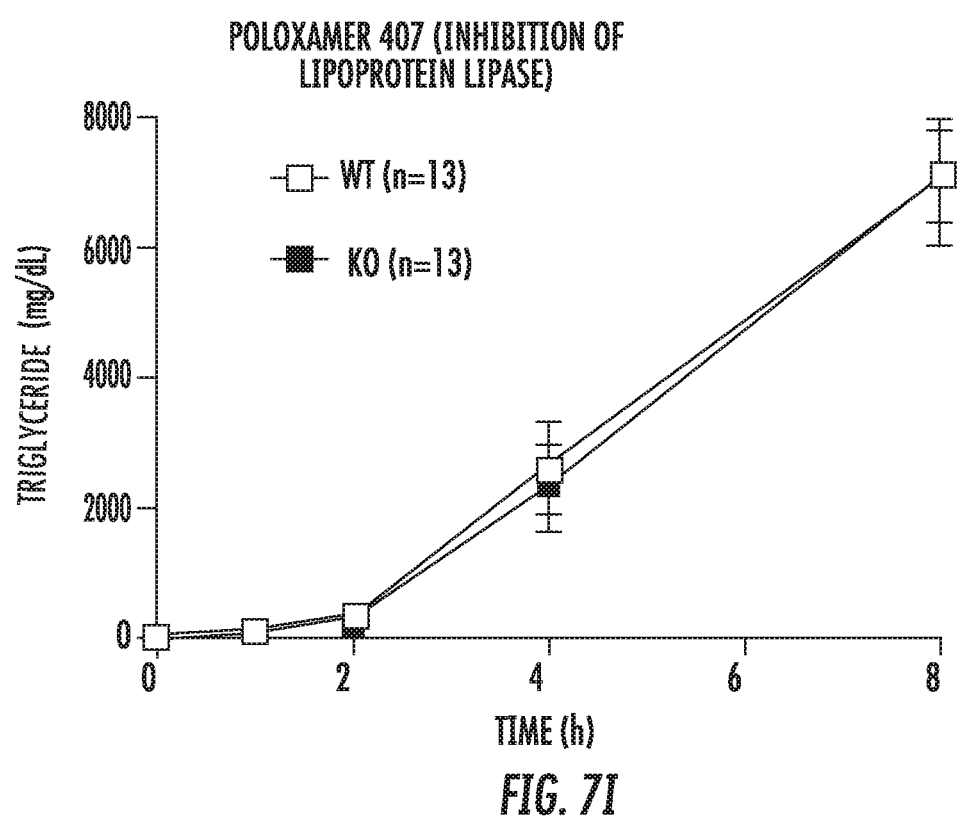
Figure 9A:
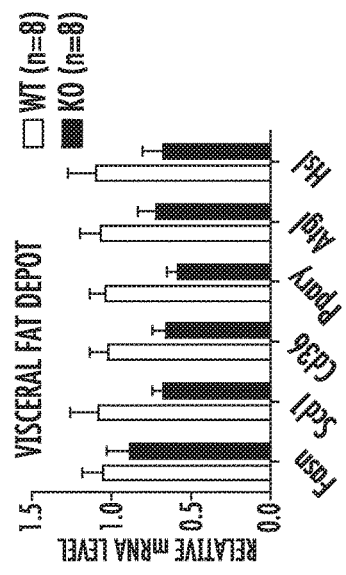
FIG. 9A-9S illustrates the reduced adipose expression of lipid synthesis and fibrotic genes in HFD-fed Ctrp1-KO mice.
Figure 9B:
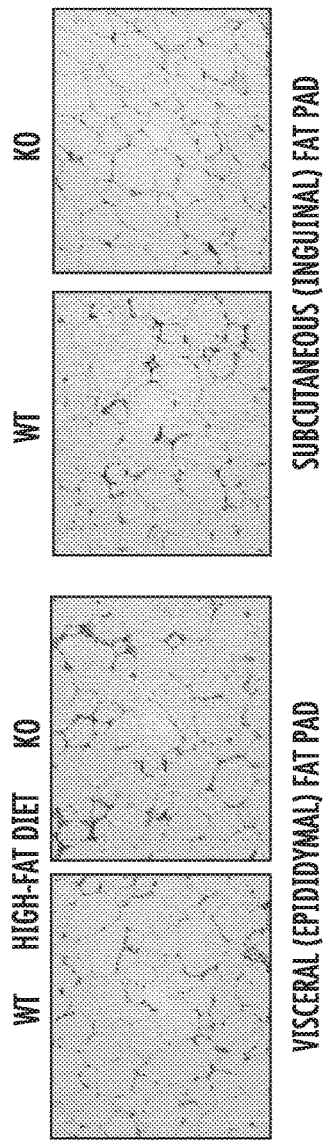
Figure 9C:
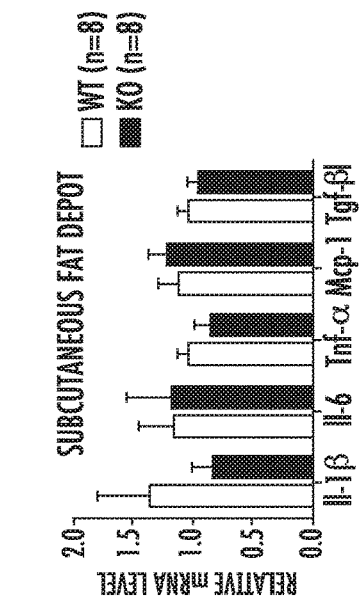
Figure 9D:
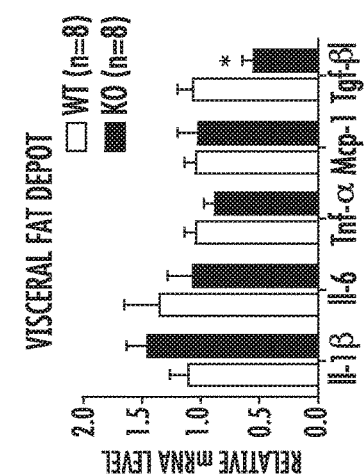
Figure 9E:
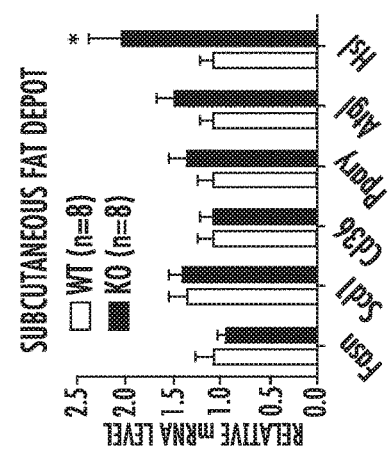
Figure 9F:
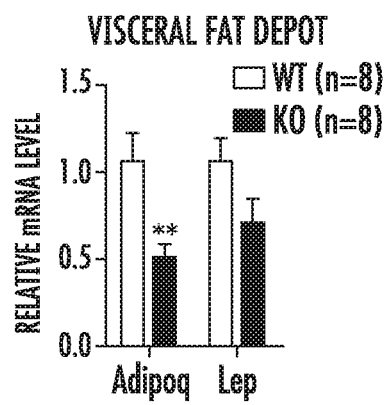
Figure 9G:
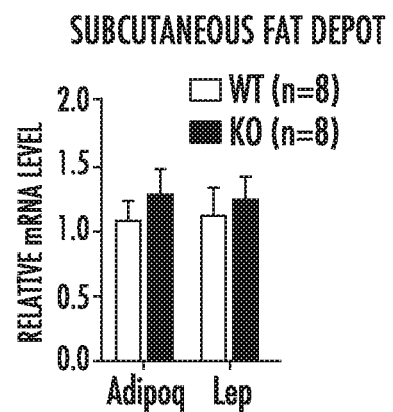
Figure 9H:
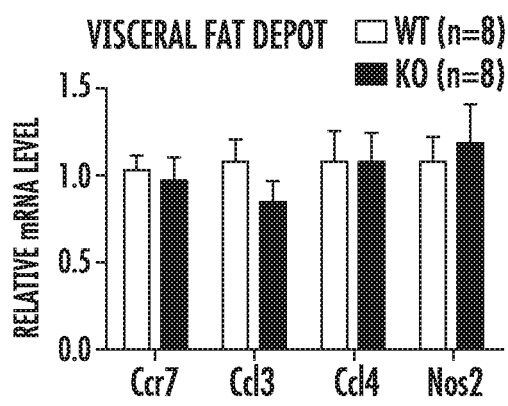
Figure 9I:
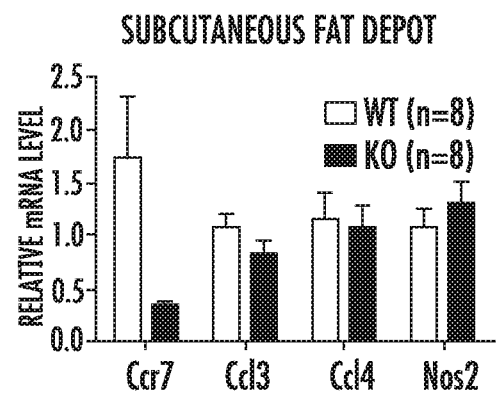
Figure 10A:
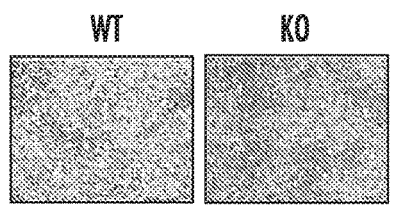
FIG. 10A-10O illustrates hepatic and circulating lipid levels are reduced in HFD-fed Ctrp1-KO male mice.
Figure 10B:
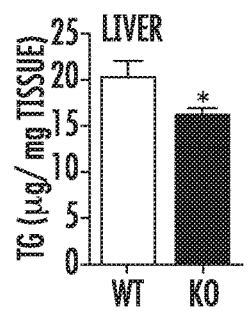
Figure 10C:
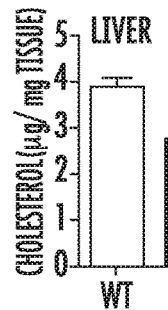
Figure 10D:
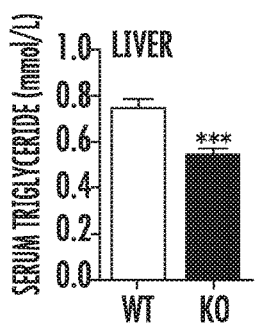
Figure 10E:
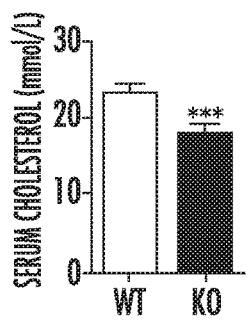
Figure 10F:
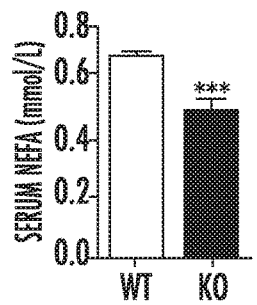
Figure 10G:
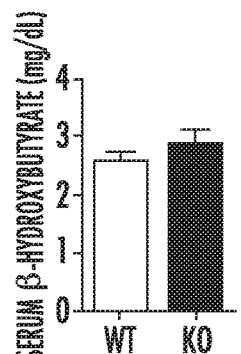
Figure 10H:
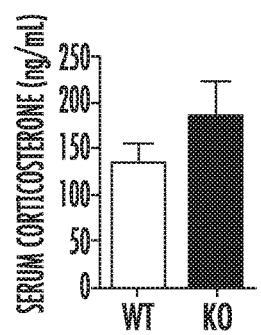
Figure 10I:
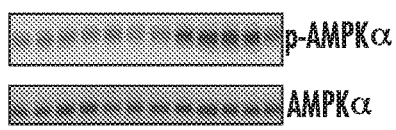
Figure 10J:
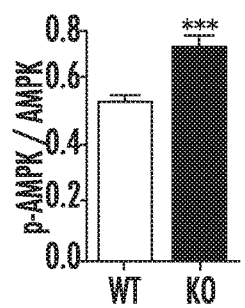
Figure 10K:
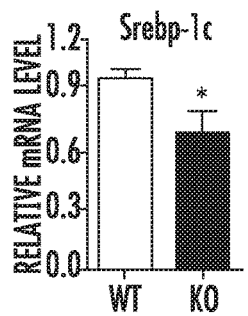
Figure 10L:
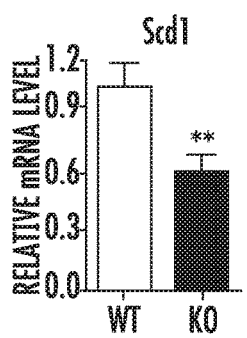
Figure 10M:
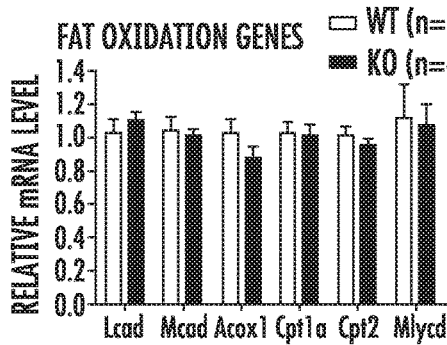
Figure 10N:
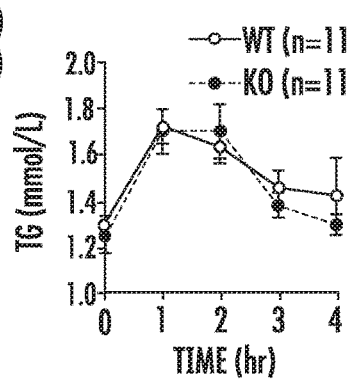
Figure 10O:
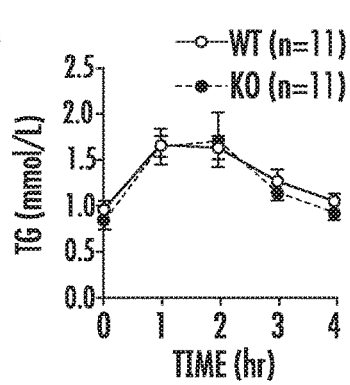

One of the most striking phenotypes revealed by this study was the enlargement of the liver and the development of prominent steatosis in Ctrp1-KO mice fed an LFD (FIG. 5). Several mechanisms could account for the accumulation of liver triglycerides in the Ctrp1-KO animals: 1) Decreased hepatic fat oxidation; 2) Increased hepatic triglyceride synthesis; 3) Decreased triglyceride export from the liver in the form of VLDL-triglyceride particles; 4) Increased lipid flux into the liver. We examined which of these pathways might be altered in the absence of CTRP1. With regard to hepatic fat oxidation, we did not observe any differences in the expression of hepatic fat oxidation genes (FIG. 6), nor did we observe changes in serum ketones (β-hydroxybutyrate acids) levels, a surrogate indicator of hepatic fat oxidation. Further, the respiratory exchange ratio (RER) did not indicate any differences in fat oxidation between WT and KO mice. In the liver, triglyceride is synthesized via the glycerol phosphate pathway (1) through the sequential acylation of glycerol-3 phosphate, lysophosphatidic acid, and diacylglycerol by multiple isoforms of GPAT, AGPAT, and DGAT enzymes. With the exception of increased Agpat1 expression, the expression of genes involved triglyceride synthesis or de novo lipogenesis was not found to be different between genotypes. The use of a lipoprotein lipase inhibitor (poloxamer 407) to block triglyceride hydrolysis and uptake into peripheral tissues allowed us to measure the accumulation of serum triglycerides due to hepatic VLDL-triglyceride export and no differences in the rate of triglyceride export were observed between WT and Ctrp1-KO mice (FIG. 7). Finally, we performed lipid tolerance tests to determine whether CTRP1 deficiency alters the clearance rate of ingested lipids. Interestingly, loss of CTRP1 enhanced lipid clearance relative to WT controls (FIG. 7). Ingested lipids (triglycerides and free fatty acids) are normally delivered to the liver from the intestine via the lymphatic system, in the form of chylomicrons, to be repackaged into VLDL-triglyceride particles before being exported out to peripheral tissues. Thus, an increased rate of lipid clearance, without changes in hepatic VLDL-triglyceride export, likely contributes to the accumulation of triglycerides seen in the liver of Ctrp1-KO mice fed an LFD.

In our recent description of the CTRP1 transgenic mouse model, we illustrated that the protective role of CTRP1 was only revealed when mice were challenged with HFD to induce obesity and insulin resistance. We subjected the Ctrp1-KO animals to a HFD to determine whether the loss of Ctrp1 might amplify the effects of the HFD. Given that CTRP1 overexpression attenuates metabolic dysfunction induced by HFD and that Ctrp1-KO mice develop insulin resistance and fatty liver on a LFD, we expected the KO animals to develop pronounced glucose intolerance and an even greater degree of liver steatosis when challenged with a HFD. Surprisingly, we observed the opposite. Ctrp1-KO mice consuming a HFD were leaner, with reduced body weight and adiposity compared to WT littermate controls (FIG. 8). Glucose and insulin tolerance were not significantly different between genotypes, suggesting that the HFD-fed Ctrp1-KO animals were not more insulin resistant than their WT counterparts. An unexpected finding was that Ctrp1-KO mice were significantly more active, during both the light and dark phases of the photocycle when compared to HFD-fed WT littermate controls. The activity levels of HFD-fed Ctrp1-KO mice were comparable to KO animals fed a LFD (Table 3); in contrast, HFD-fed WT mice had significantly lower physical activity levels compared to LFD-fed WT animals. Food intake, however, was not different between genotypes on HFD. How the loss of CTRP1 enhances physical activity in the context of HFD is presently unknown. Increased physical activity without changes in caloric intake likely contributed, at least in part, to the lower weight gain and adiposity seen in HFD-fed Ctrp1-KO animals relative to WT controls.

TABLE 1

| Low-fat diet | Male | | | Female | | |
|---|---|---|---|---|---|---|
| | WT (n = 12) | KO (n = 9) | p-value | WT (n = 13) | KO (n = 10) | p-value |
| Food intake (g) | 4.690 ± 0.1986 | 4.551 ± 0.2407 | ns | 4.691 ± 0.2746 | 4.808 ± 0.2631 | ns |
| $VO_2$ (mL/kg-LM/hr) | 4544 ± 72.35 | 4786 ± 114.9 | ns | 5537 ± 116.9 | 5488 ± 142.6 | ns |

TABLE 1-continued

| | | | | | | |
|---|---|---|---|---|---|---|
| VCO$_2$ (mL/kg-LM/hr) | 4309 ± 84.02 | 4484 ± 95.31 | ns | 5252 ± 105.5 | 5252 ± 153.2 | ns |
| Respiratory exchange ratio (RER) | 0.9484 ± 0.01153 | 0.9376 ± 0.008531 | ns | 0.9498 ± 0.01204 | 0.9575 ± 0.01583 | ns |
| Energy expenditure (kcal/kg-LM/hr) | 22.64 ± 0.3630 | 23.78 ± 0.5492 | ns | 27.59 ± 0.5587 | 27.41 ± 0.7088 | ns |
| Physical activity (beam breaks) | 42724 ± 3313 | 39886 ± 2106 | ns | 75971 ± 4388 | 82086 ± 6942 | ns |

| | Male | | | Female | | |
|---|---|---|---|---|---|---|
| High-fat diet | WT (n = 11) | KO (n = 11) | p-value | WT (n = 13) | KO (n = 10) | p-value |
| Food intake (g) | 2.722 ± 0.1088 | 2.865 ± 0.08533 | ns | 2.388 ± 0.09373 | 2.305 ± 0.08192 | ns |
| VO$_2$ (mL/kg-LM/hr) | 4860 ± 75.24 | 4758 ± 58.97 | ns | 5382 ± 90.54 | 5343 ± 99.06 | ns |
| VCO$_2$ (mL/kg-LM/hr) | 3701 ± 56.74 | 3610 ± 47.73 | ns | 4330 ± 61.52 | 4302 ± 73.03 | ns |
| Respiratory exchange ratio (RER) | 0.7616 ± 0.002731 | 0.7587 ± 0.002106 | ns | 0.8050 ± 0.003875 | 0.8055 ± 0.004440 | ns |
| Energy expenditure (kcal/kg-LM/hr) | 23.10 ± 0.3555 | 22.60 ± 0.2828 | ns | 25.87 ± 0.4191 | 25.68 ± 0.4646 | ns |
| Physical activity (beam breaks) | 27449 ± 1736 | 37192 ± 2563 | ** | 43631 ± 3942 | 57716 ± 5570 | * |

In contrast to the LFD-fed Ctrp1-KO mice that developed fatty liver, KO animals consuming a HFD unexpectedly had reduced hepatic steatosis compared to WT controls (FIG. 10). Both hepatic and serum triglyceride levels were reduced in HFD-fed Ctrp1-KO mice. Unlike the LFD-fed KO mice, lipid tolerance testing did not reveal any differences in the rate of triglyceride and free fatty acid clearance between HFD-fed WT and KO animals. Reduced body weight and adiposity likely contributed, in part, to decreased liver steatosis seen in the HFD-fed Ctrp1-KO animals. Other factors contributing to this phenotype are likely related to the reduced hepatic expression of lipid synthesis genes (Srebp-1c and Scd1) and an increase in the relative phosphorylation and activation of AMPK (FIG. 10), both of which could contribute to the lower hepatic lipid content observed in the Ctrp1-KO animals. Although less adiposity, a healthier liver, and improved serum lipid levels frequently associate with an improved systemic metabolic profile, the observed reduction in adiposity, hepatic steatosis, and serum lipid levels seen in Ctrp1-KO mice (FIGS. 8 and 10) did not appear to affect systemic glucose metabolism, as indicated by lack of differences in glucose and insulin tolerance tests between genotypes (FIG. 8).

Adipose tissue inflammation and fibrosis, particularly in the context of obesity, are known to alter the expression and secretion of adipokines; this in turn has systemic effects on energy metabolism and insulin sensitivity. Given that CTRP1 is abundantly expressed in adipose tissue, we assessed the impact of CTRP1 deficiency on the expression of genes involved in lipid uptake and synthesis, inflammation, macrophage polarization, and tissue fibrosis. With the exception of reduced fibrotic collagen gene expression, loss of CTRP1 had a relatively minor impact on adipose tissue function when mice were fed an LFD (FIG. 4). In the context of HFD-induced metabolic stress, however, the expression of multiple lipid metabolism genes (Scd1, Cd36, Ppar-γ) was significantly reduced in the adipose tissue of Ctrp1-KO mice (FIG. 9). The adipose expression and circulating levels of pro-fibrotic TGF-β were also reduced in Ctrp1-KO animals. Since TGF-β is a potent inducer of fibrotic collagen gene expression, its reduction in mRNA and circulating levels likely contributed to the decreased expression of Col3 and Col6. While adipose mass and fibrosis are known to impact systemic metabolism, their reductions in Ctrp1-KO mice were likely insufficient to alter systemic insulin action (FIG. 10).

Adiponectin is a widely studied insulin-sensitizing adipokine with pleiotropic metabolic function. Interestingly, serum adiponectin levels were lower in both LFD and HFD-fed Ctrp1-KO mice compared to WT controls. Although serum adiponectin levels were reduced in LFD-fed Ctrp1-KO mice (FIG. 4), these changes are unlikely to account for the insulin resistance and fatty liver phenotypes observed in our study. Three independent adiponectin KO mouse lines, when fed a chow diet comparable to LFD, are largely indistinguishable from WT controls, with minimum or no detectable metabolic abnormalities. When challenged with a HFD, different adiponectin KO mouse lines develop variable, and relatively mild, degrees of insulin resistance compared to WT controls. In our study, insulin sensitivity was not different between HFD-fed WT and Ctrp1-KO mice despite reduced serum levels of adiponectin (FIGS. 8 and 9).

Given the increasing appreciation of sex-dependent differences in metabolic disease phenotypes and severity (31, 49), we included female WT and KO animals in our studies. Unlike male mice, Ctrp1-KO female mice consuming a control LFD did not develop insulin resistance, glucose intolerance, or fatty liver. When challenged with a HFD, the metabolic phenotypes (body weight, adiposity, energy expenditure, physical activity, and glucose and insulin tolerance) of Ctrp1-KO female mice were indistinguishable from female WT littermate controls (Table 2). Thus, loss of CTRP1 likely contributes to dysregulated metabolism in a sex-dependent manner. Given the myriad physiological roles of sex hormones, this is neither unexpected nor surprising as the metabolic phenotypes of many loss-of-function mouse models are often manifested in male, but not female, animals.

TABLE 2

| | Male | | | Female | | |
|---|---|---|---|---|---|---|
| Low-fat diet (LFD) | WT n = 12 | KO n = 8 | p-Value | WT n = 17 | KO n = 8 | p-Value |
| Body weight (g) | 38.2825 ± 0.694 | 36.92125 ± 0.840 | ns | 29.01 ± 0.780 | 29.72 ± 1.210 | ns |
| Gonadal fat mass (g) | 0.955 ± 0.025 | 0.77875 ± 0.036 | *** | 0.5159 ± 0.04220 | 0.4400 ± 0.05910 | ns |
| Gonadal fat mass/body weight | 0.0249 ± 0.0005604 | 0.02104 ± 0.0006512 | *** | 0.01739 ± 0.001096 | 0.01442 ± 0.001489 | ns |
| Inguinal fat mass (g) | 0.739 ± 0.052 | 0.645 ± 0.035 | ns | 0.3441 ± 0.02919 | 0.3750 ± 0.03423 | ns |

TABLE 2-continued

| | WT | KO | p-Value | WT | KO | p-Value |
|---|---|---|---|---|---|---|
| Inguinal fat mass/body weight | 0.01926 ± 0.001213 | 0.01746 ± 0.0008242 | ns | 0.01160 ± 0.0007863 | 0.01248 ± 0.0008185 | ns |
| Liver weight (g) | 1.983 ± 0.1271 | 2.445 ± 0.1696 | | 1.405 ± 0.07098 | 1.653 ± 0.1524 | ns |
| Liver weight/body weight | 0.05155 ± 0.002590 | 0.06592 ± 0.003748 | ** | 0.04801 ± 0.001372 | 0.05501 ± 0.003409 | * |
| Gastrocnemius muscle (g) | 0.121 ± 0.005 | 0.116 + 0.005 | ns | ND | ND | NA |
| Gastrocnemius muscle/body weight | 0.003163 + 0.0001215 | 0.003148 + 0.0001273 | ns | ND | ND | NA |
| Heart (g) | 0.169 ± 0.009 | 0.158 ± 0.007 | ns | 0.1488 ± 0.005871 | 0.1475 ± 0.0075 | ns |
| Heart/tibia length | 0.009313 ± 0.0004806 | 0.008790 ± 0.0003024 | ns | 0.008234 ± 0.0003175 | 0.008154 ± 0.0004050 | ns |
| Fasting blood glucose (mg/dL) | 192.083 ± 4.914 | 182 ± 6.059 | ns | 158.0 ± 4.263 | 155.4 ± 8.181 | ns |
| Tibia length (mm) | 18.147 ± 0.190 | 17.890 ± 0.181 | ns | 18.07 ± 0.09276 | 18.09 ± 0.2816 | ns |

| High-fat diet (HFD) | WT n = 11 | KO n = 10 | p-Value | WT n = 15 | KO n = 10 | p-Value |
|---|---|---|---|---|---|---|
| Body weight (g) | 55.04 ± 1.089 | 48.85 ± 0.4851 | **** | 53.53 ± 1.816 | 50.20 ± 1.278, n = 10 | ns |
| Gonadal fat mass (g) | 0.6082 ± 0.05129 | 0.600 ± 0.6703 | ns | 2.199 ± 0.09796 | 1.916 ± 0.1258 | ns |
| Gonadal fat mass/body weight | 0.01104 ± 0.0009028 | 0.01229 ± 0.001357 | ns | 0.04107 ± 0.001234 | 0.03798 ± 0.001984 | ns |
| Inguinal fat mass (g) | 1.256 ± 0.04535 | 0.9150 ± 0.03198 | **** | 1.202 ± 0.04528 | 1.112 ± 0.06734 | ns |
| Inguinal fat mass/body weight | 0.02281 ± 0.0006551 | 0.01874 ± 0.0006571 | *** | 0.02258 ± 0.0007765 | 0.02222 ± 0.001315 | ns |
| Liver weight (g) | 3.810 ± 0.1604 | 3.892 ± 0.2103 | ns | 2.149 ± 0.2036 | 2.174 ± 0.1756 | ns |
| Liver weight/body weight | 0.06920 ± 0.002455 | 0.07957 ± 0.004000 | | 0.03911 ± 0.002605 | 0.04286 ± 0.002777 | ns |
| Heart (g) | 0.2291 ± 0.009672 | 0.2190 ± 0.01602 | ns | 0.1540 ± 0.007091 | 0.1470 ± 0.002134 | ns |
| Heart/tibia length | 0.01279 ± 0.0004742 | 0.01223 ± 0.0008627 | ns | 0.008605 ± 0.0003912 | 0.008196 ± 0.0001319 | ns |
| Fasting blood glucose (mg/dL) | 175.7 ± 4.357 | 176.5 ± 9.165 | ns | 183.0 ± 4.508 | 194.6 ± 7.162 | ns |
| Tibia length (mm) | 17.90 ± 0.2372 | 17.89 ± 0.08167 | ns | 17.89 ± 0.1206 | 17.95 ± 0.1503 | ns |

In summary, our results support an important role for CTRP1 in metabolic homeostasis. The contribution of CTRP1 to systemic glucose and lipid metabolism is sex-dependent and relies on the specific metabolic and dietary context. When fed an LFD, loss of CTRP1 impaired hepatic lipid metabolism (resulting in fatty liver) and systemic insulin sensitivity. In the context of HFD, CTRP1 deficiency attenuated diet-induced obesity and fatty liver. Our study underscores the complex regulation of whole-body metabolism by secreted regulators of the CTRP family.

Figure 11A:
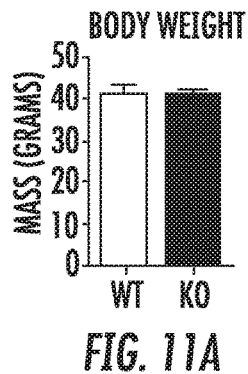
FIG. 11A-11J illustrates CTRP-KO mice fed a low-fat diet (Cohort 6) with overnight fast. These mice were 52 weeks old and on a low-fat diet for 47 weeks.
Figure 11B:
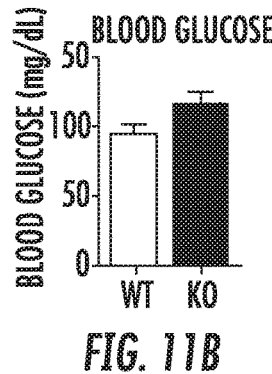
Figure 11C:
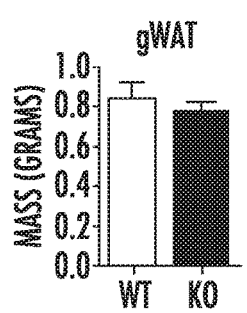
Figure 11D:
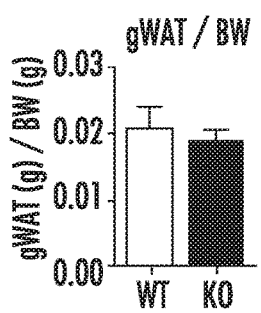
Figure 11E:
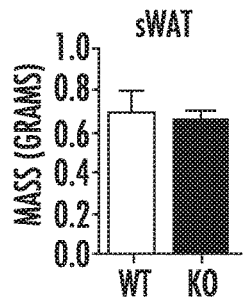
Figure 11F:
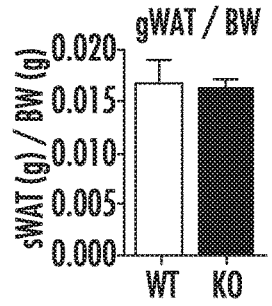
Figure 11G:
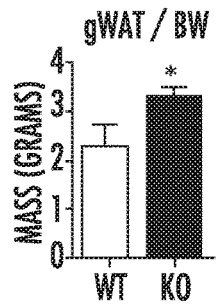
Figure 11H:
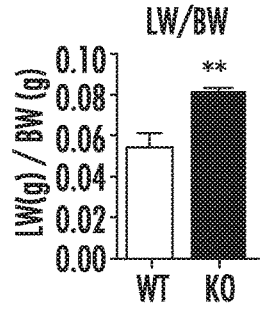
Figure 11I:
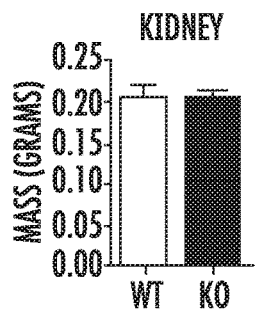
Figure 11J:
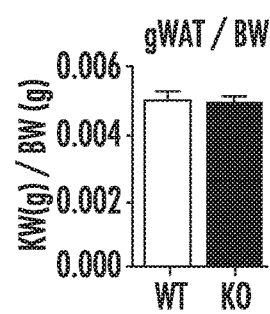
Figure 12A:
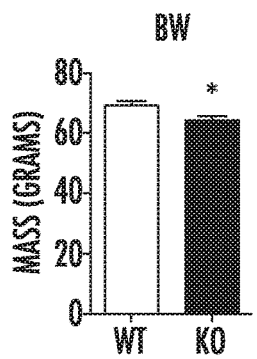
FIG. 12A-12J illustrates CTRP1 KO HFD Male Mice (Cohort 2) with overnight fast. These mice were 62 weeks; WT is 8; HFD is 56 weeks; and KO is 17.
Figure 12B:
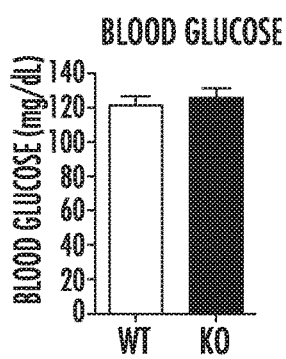
Figure 12C:
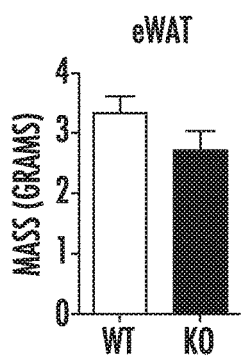
Figure 12D:
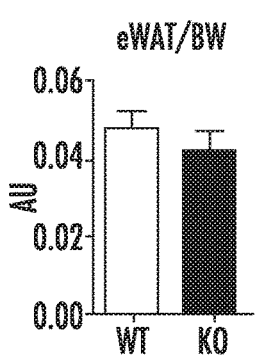
Figure 12E:
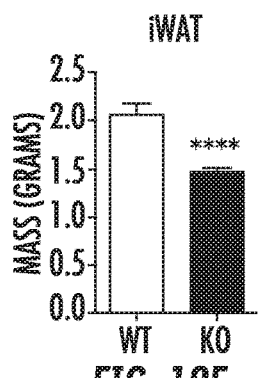
Figure 12F:
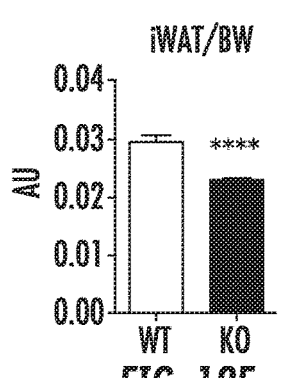
Figure 12G:
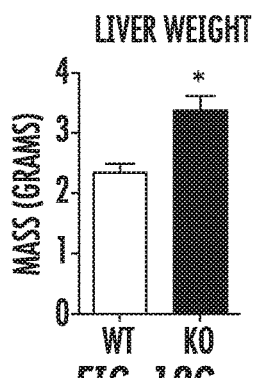
Figure 12H:
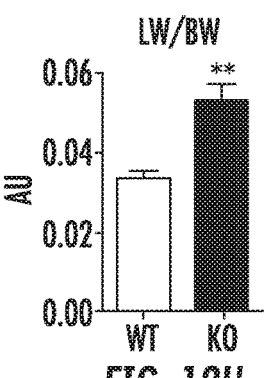
Figure 12I:
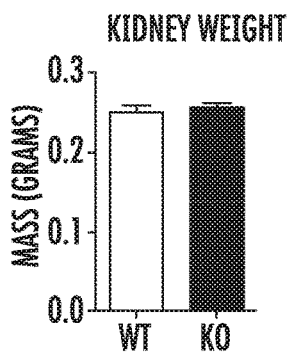
Figure 12J:
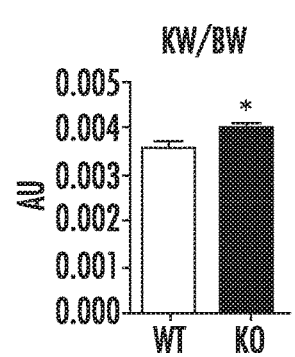

Regarding the in vivo function of CTRP1, especially as it relates to lipid metabolism in liver using a genetic mouse model in which the Ctrp1 gene was deleted, the inventors made the following discovery. Specifically, CTRP1 knock-out (KO) mice, were fed a control low-fat diet and fasted overnight. Observed was a dramatic and striking increase in liver weight, whether it was liver mass (FIG. 11G) or the ratio of liver mass to body weight (FIG. 11H). Other tissues, however, were not different in weight; these include total body weight (FIG. 11A), gonadal (gWAT) and subcutaneous (sWAT) white adipose tissue (FIGS. 11C-F), and kidney weight (FIG. 11 I, J). The liver phenotypes were even more striking when the CTRP1-KO mice were fed a high-fat diet to induce obesity. In this case, overnight fasted CTRP1 deficient mice also have a pronounced liver enlargement (FIG. 12G-H). In contrast to the liver, we observed a modest reduction in total body weight (FIG. 12A) and decreased iguinal (subcutaneous) fat depot (iWAT, FIG. 12E-F).

Figure 13B:
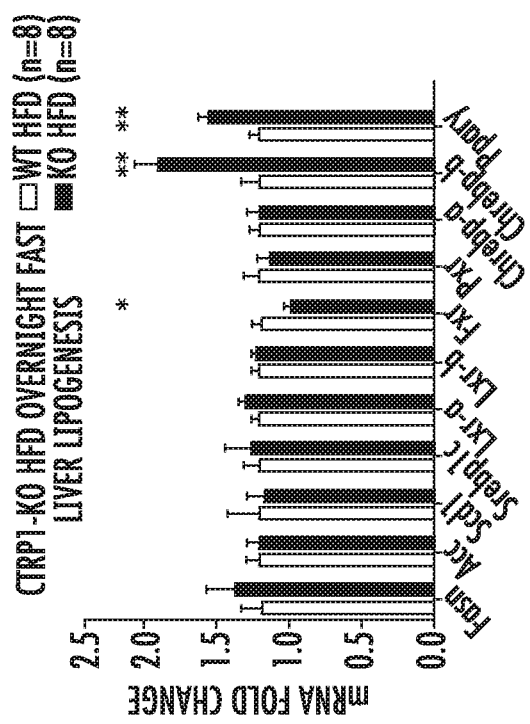
Figure 13A:
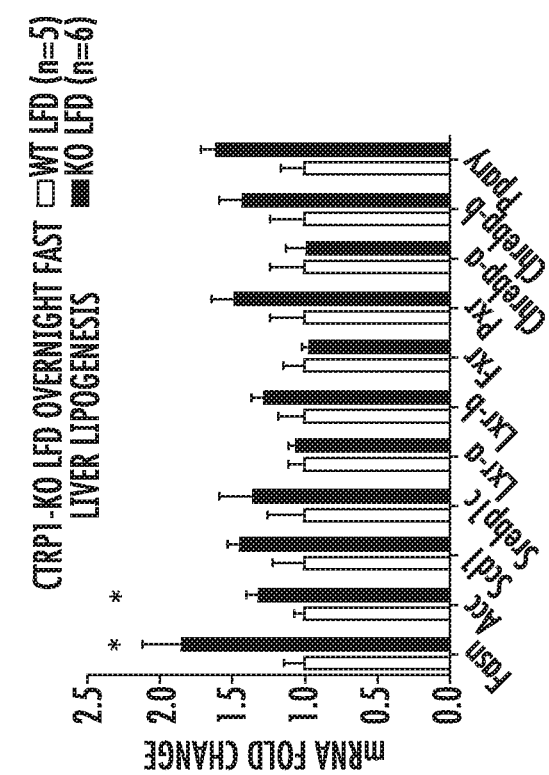

During the overnight fast, the inventors believe lipids from the adipose tissue get mobilized and shunted to the liver for oxidation. Energy derived from fat oxidation enables liver to make glucose during fasting to maintain normal blood glucose levels. One possible mechanism that can account for the enlargement of liver in response to the overnight fast is the reduction in fat oxidation. Indeed, expression of many of the fat oxidation genes in liver were significantly down-regulated in overnight fasted CTRP1 deficient animals (FIG. 13D). In contrast, the expression of genes involved in lipid synthesis was up-regulated in CTRP1 KO mice (FIG. 13A-B).

The inventors believe, based on genetic mouse model data, there is an important role for CTRP1 hormone in regulating hepatic lipid metabolism and the therapeutic potential of using recombinant CTRP1 protein to reduce lipid accumulation in liver in the context of non-alcoholic fatty liver disease (NAFLD).

Examples/Methods

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Animals

The Ctrp1 KO (−/−) mouse strain used for this research project (B6; 129S5-C1qtnf1$^{tm1Lex}$/Mmucd, identification number 032164-UCD) was obtained from the Mutant Mouse Regional Resource Center (MMRRC), an NCRR-NIH funded strain repository, and was donated to the MMRRC by Genentech, Inc. The Ctrp1 gene is located on mouse chromosome 11 and comprises 4 exons. The largest exon, exon 4 (which codes for 61% of the full-length protein), was targeted by homologous recombination. A total of 679 bp, spanning the coding region of exon 4 and a portion (162 bp) of the 3'UTR, was deleted. Heterozygous mice were recovered from cryo-preserved embryos. Since the ES cells were derived from the 129S5/Sv mouse strain, we backcrossed Ctrp1 KO mice to the C57BL/6J genetic background for >6 generations. The Ctrp1 KO mice were viable and fertile. Genotyping primers for the Ctrp1 wild-type (WT) allele were as follows: forward (DNA063-1), 5'-GGTTCTA-CAGGTCC CAGGG-3' (SEQ ID NO: 2); and reverse (DNA063-2), 5'-GTGATGTAGGTGTCGAACTCG-3' (SEQ ID NO: 3). The expected size of the WT amplification product was 458 bp. Genotyping primers for the Ctrp1-KO allele were as follows: forward (Neo-3a), 5'-GCAGCG-CATCGCCTTCTATCG-3' (SEQ ID NO: 4) and reverse (DNA063-31) 5'-GGAAGTCCCTCTCACGTGTC-3' (SEQ ID NO: 5). The expected size of the KO amplification product was 1100 bp. To confirm the presence or absence of Ctrp1 mRNA in the adipose tissue of WT and KO mice, we performed semi-quantitative PCR analysis using the following primer pair: forward, 5'-GTGAGGACCTCCC-CACTTCT-3' (SEQ ID NO: 6) and reverse, 5'-GACCAGGTAGCCA CTGAAGG-3' (SEQ ID NO: 7). The expected size of the amplification product was 632 bp. All Ctrp1-KO (−/−) and WT (+/+) littermate controls used in this study were generated by intercrossing Ctrp1 heterozygous (+/−) mice. Male and female Ctrp1 KO mice and WT littermate controls were housed in polycarbonate cages on a 12-h light-dark photocycle with ad libitum access to water and food. Mice were fed a high-fat diet (HFD; 60% kcal derived from fat, Research diets; D12492) or a matched control low-fat diet (LFD; 10% kcal derived from fat, Research diets; D12450B). Diet was provided for a period of 24 weeks, beginning at 6 weeks of age. All animal protocols were approved by the Institutional Animal Care and Use Committee of The Johns Hopkins University School of Medicine.

CTRP1 ELISA

An ELISA specific for mouse CTRP1 was obtained from BioVendor R&D, Czech Republic. The assay was carried out according to manufacturer's instructions.

Body Composition Analysis

Body composition analyses for fat and lean mass were performed on mice at 19-24 weeks using Echo-MRI-100 (Echo Medical Systems, Waco, Tex.) at The Johns Hopkins University School of Medicine mouse phenotyping core facility. Lean mass was used to normalize the indirect calorimetry data.

Indirect Calorimetry

LFD-fed and HFD-fed WT and Ctrp1-KO mice at 19-24 weeks of age were used for simultaneous assessments of daily body weight change, food intake (corrected for spillage), physical activity, and whole-body metabolic profile in the Comprehensive Laboratory Animal Monitoring System (CLAMS) system (Columbus Instruments). Data were collected for 3-4 days to confirm that mice were acclimated to the calorimetry chambers (indicated by stable body weights, food intake, and diurnal metabolic patterns), and data were analyzed from the fourth day. Rates of oxygen consumption ($VO_2$, normalized to mL·lean $kg^{-1} \cdot h^{-1}$) and carbon dioxide production ($VCO_2$; mL·lean $kg^{-1} \cdot h^{-1}$) in each chamber were measured every 24 min throughout the studies. Respiratory exchange ratio ($RER=VCO_2/VO_2$) was calculated by CLAMS software (version 4.02) to estimate relative oxidation of carbohydrates (RER=1.0) vs. fats (RER~0.7), not accounting for protein oxidation. Energy expenditure (EE) was calculated as $EE=VO_2 \times [3.815+(1.232 \times RER)]$ (29) and normalized for lean body mass (kcal·lean $kg^{-1} \cdot h^{-1}$) as recommended (2). Physical activities were measured by infrared beam breaks in the metabolic chamber. Average metabolic values were calculated per mouse and averaged across mice for statistical analysis by Student's t-test.

Intraperitoneal Glucose and Insulin Tolerance Test

Mice were fasted for 6 h before glucose injection. Glucose was injected intraperitoneally (i.p.) into mice at a dose of 1 mg/g body weight. Blood glucose was measured at 0, 15, 30, 60, and 120 min post glucose injection using a glucometer (BD Pharmingen, Franklin Lakes, N.J.). Fasting serum insulin levels were measured using an ELISA kit (Millipore, Billerica, Mass.). For insulin tolerance tests, food was removed 2 h before insulin injection. Insulin was injected i.p. at a dose of 0.75 U/kg body weight for LFD-fed mice and 1 or 1.5 U/kg body weight for HFD-fed mice, and blood glucose was measured at 0, 15, 30, 60, and 90 min post insulin injection as described above. The homeostatic model assessment of insulin resistance (HOMA-IR) was calculated based on fasting glucose and insulin concentrations as HOMA-IR=(fasting glucose [mM]×fasting insulin [microunits/mL])/22.5 (27). This surrogate index provides a reasonable approximation of the degree of insulin resistance and has been validated against the reference standard glucose clamp for rats (5) and mice (21).

Lipid Tolerance Test

For lipid tolerance tests (LTT), mice were fasted for 12 h and then gavaged with 20% emulsified Intralipid (soybean oil; Sigma; 10 µL/g of body weight). Sera were collected via tail bleed using a Microvette® CB 300 (Sarstedt) at 0, 1, 2, 3, and 4 h post-injection. Serum levels of non-esterified free fatty acids (NEFA) and triglycerides were quantified using kits from Wako Diagnostics and Infinity Triglycerides (Thermo Scientific), respectively.

Hepatic VLDL-Triglyceride Quantification

To measure the hepatic VLDL-triglyceride production rate, a separate cohort of LFD-fed WT and Ctrp1-KO mice were given an intraperitoneal injection of 1000 mg/kg poloxamer 407 (Sigma) in saline ~4 h into the light cycle, as described by Millar et al. (30) and our previous study (37). Poloxamer 407 inhibits lipoprotein lipase activity and blocks triglyceride hydrolysis, thus allowing VLDL-triglycerides to accumulate over time and enables the calculation of hepatic VLDL-triglyceride secretion rates (30). Serum samples were collected at 0, 1, 2, 4, and 8 h and analyzed for triglyceride concentration. Serum levels of triglycerides were quantified using the Infinity Triglycerides kit (Thermo Scientific).

Tissue Collection

Liver, white adipose tissue (perigonadal/visceral and inguinal/subcutaneous), and skeletal muscle samples were immediately harvested from euthanized mice and flash-frozen into liquid nitrogen. Homogenized tissue lysates were prepared in RIPA lysis buffer (50 mM Tris-HCl pH 7.4, 150 mM NaCl, 1 mM EDTA, 1% Triton×100, and 0.25% deoxycholate) containing protease inhibitors (Complete Mini, Roche) and phosphatase inhibitors (PhosSTOP, Roche). Tissue lysates were centrifuged at 10,000 rpm for 20 minutes at 4° C. for 20 minutes. Supernatants were collected and protein content was quantified using the Pierce BCA Protein Assay Kit (Thermo Scientific).

Histology

WT and Ctrp1-KO mouse tissues were fixed overnight in 10% formalin at 4° C. Fixed tissues were embedded in paraffin, sectioned, and stained with hematoxylin and eosin (H & E) at the Histology Reference Laboratory at The Johns Hopkins University School of Medicine.

Serum and Blood Chemistry Analysis

Mouse serum was harvested by retro-orbital bleeding at the time of euthanasia. Samples were separated using a Microvette® CB 300 (Sarstedt, Numbrecht, Germany) and centrifuged at 10,000×g for 5 min. Glucose concentrations were determined at the time of collection with a glucometer (BD Pharmingen). Serum lipid levels were measured by the Mouse Pathology and Phenotyping Core at The Johns Hopkins University School of Medicine. Insulin, adiponectin, leptin, TNF-α, MCP-1, IL-1β, and IL-6 were measured using Millipore kits. Serum TGF β-1 was measured using an Abcam kit and CTRP1 was measured using a kit from BioVendor R&D.

Lipid Extraction from Liver Tissue

Lipid extraction was performed as previously described (37). In brief, liver (50 mg) was homogenized in 500 µL of distilled water. 200 μL of the homogenate was collected for lipid extraction, mixed with 1 mL of choloroform:methanol (2:1), and centrifuged at 1700 rpm for 5 min at 4° C., and the chloroform phase was collected and dried in a vacuum. Samples were re-suspended in tert-butanol:MeOH:Triton-X100 (3:1:1) before determining triacylglycerol and cholesterol content using commercially available colorimetric kits (Thermo Scientific).

Western Blot Analysis

Western blot analyses were carried out and quantified as previously described (41), using antibodies specific to GLUT4, AMPKα, AKT, phospho-AKT (Ser-473), and phospho-AMPKα (Thr-172) (Cell Signaling Technology). PGC1α antibody was obtained from Abcam (cat #ab54481).

Quantitative Real-Time PCR Analysis

Total RNA was isolated from tissues using Trizol® (Thermo Scientific) and reverse transcribed using the GoScript Reverse transcription system (Promega). Real-time PCR primers for gluconeogenic genes (G6Pc, Pck1) (39), triglyceride synthesis genes (Gpat, Agpat, Dgat) (37), de novo lipogenesis, fat oxidation and adipokine genes (Acc1, Fasn, Srebp1, Acox1, Cpt1, Cpt2, Lcad, Mcad, Adipoq, Lep) (55), fibrotic genes (Col1, Col3, Col6) (22), and inflammatory genes (Il-1β, Il-6, Tgf-β) have been previously published. Other primer sequences used in this study are listed in Table 1. Quantitative real-time PCR analyses were performed on a CFX Connect system (Bio-Rad Laboratories, Hercules, Calif.). Samples were analyzed in 20 μL reactions with SyBR® Green PCR Master Mix (Applied Biosystems, Invitrogen) per the manufacturer's directions. Data were normalized to 36B4 (adipose tissue), 18S rRNA (skeletal muscle), and β-actin (liver) and expressed as relative mRNA levels using the ΔΔCt method (23).

TABLE 3

| Gene | Forward primer | Reverse primer |
| --- | --- | --- |
| 36B4 | AGATTCGGGATATGCTGTTGGC (SEQ ID NO: 8) | TCGGGTCCTAGACCAGTGTTC (SEQ ID NO: 9) |
| Hmgcr | CTTGTGGAATGCCTTGTGATTG (SEQ ID NO: 10) | AGCCGAAGCAGCACATGAT (SEQ ID NO: 11) |
| Sqle | ATAAGAAATGCGGGGATGTCAC (SEQ ID NO: 12) | ATATCCGAGAAGGCAGCGAAC (SEQ ID NO: 13) |
| Abca1 | GCTGCAGGAATCCAGAGAAT (SEQ ID NO: 14) | CATGCACAAGGTCCTGAGAA (SEQ ID NO: 15) |
| Apoc2 | AGGTTCCGGCTTGATGAGAA (SEQ ID NO: 16) | AGTGGGTTGGCAGGCTTTAT (SEQ ID NO: 17) |
| Apoe | CTGACAGGATGCCTAGCCG (SEQ ID NO: 18) | CGCAGGTAATCCCAGAAGC (SEQ ID NO: 19) |
| Vldlr | GAGCCCCTGAAGGAATGCC (SEQ ID NO: 20) | CCTATAACTAGGTCTTTGCAGATATGG (SEQ ID NO: 21) |
| Cd36 | ATGGGCTGTGATCGGAACTG (SEQ ID NO: 22) | AGCCAGGACTGCACCAATAAC (SEQ ID NO: 23) |
| Chrebp-α | CGACACTCACCCACCTCTTC (SEQ ID NO: 24) | TTGTTCAGCCGGATCTTGTC (SEQ ID NO: 25) |
| Chrebp-β | AGCGGATTCCAGGTGAGG (SEQ ID NO: 26) | TTGTTCAGGCGGATCTTGTC (SEQ ID NO: 27) |
| Fabp1 | ATGAACTTCTCCGGCAAGTACC (SEQ ID NO: 28) | GGTCCTCGGGCAGACCTAT (SEQ ID NO: 29) |
| Fatp5 | GTTCTCCCGTCCAAGACCATT (SEQ ID NO: 30) | GCTCCGTACAGAGTGTAGCAAG (SEQ ID NO: 31) |
| Fxr | GCTTGATGTGCTACAAAAGCTG (SEQ ID NO: 32) | CGTGGTGATGGTTGAATGTCC (SEQ ID NO: 33) |
| Lxr-α | AGGAGTGTCGACTTCCGCAAA (SEQ ID NO: 34) | CTCTTCTTGCCGCTTCAGTTT (SEQ ID NO: 35) |
| Lxr-β | ATAGTGGGTCACGAAGCAGC (SEQ ID NO: 36) | AGGGCAACAGAGTCGGAGAC (SEQ ID NO: 37) |
| Scd1 | CCCAGTCGTACACGTCATTTT (SEQ ID NO: 38) | CATCATTCTCATGGTCCTGCT (SEQ ID NO: 39) |
| Mlycd | CTCGGGACCTTCCTCATAAAGA (SEQ ID NO: 40) | GAATAGTTCGTTCCTCCCATGCTC (SEQ ID NO: 41) |
| Lipc | ATGGGAAATCCCCTCCAAATCT (SEQ ID NO: 42) | GTGCTGAGGTCTGAGACGA (SEQ ID NO: 43) |
| Lpl | CCCTGAAGACACAGCTGAGG (SEQ ID NO: 44) | GGCTGTACCCTAAGAGGTGG (SEQ ID NO: 45) |

TABLE 3-continued

| Gene | Forward primer | Reverse primer |
|---|---|---|
| Mcp-1 | TTAAAAACCTGGATCGGAACCAA (SEQ ID NO: 46) | GCATTAGCTTCAGATTTACGGGT (SEQ ID NO: 47) |
| Ppar-γ | CCAGAGTCTGCTGATCTGCG (SEQ ID NO: 48) | GCCACCTCTTTGCTCTGCTC (SEQ ID NO: 49) |
| Atgl | TGTGGCCTCATTCCTCCTAC (SEQ ID NO: 50) | TCGTGGATGTTGGTGGAGCT (SEQ ID NO: 51) |
| Hsl | GCTGGGCTGTCAAGCACTGT (SEQ ID NO: 52) | GTAACTGGGTAGGCTGCCAT (SEQ ID NO: 53) |
| Ccr7 | TGT ACG AGT CGG TGT GCT TC (SEQ ID NO: 54) | GGT AGG TAT CCG TCA TGG TCT TG (SEQ ID NO: 55) |
| Ccl3 | TTCTCTGTACCATGACACTCTGC (SEQ ID NO: 56) | CGTGGAATCTTCCGGCTGTAG (SEQ ID NO: 57) |
| Ccl4 | TTCCTGCTGTTTCTCTTACACCT (SEQ ID NO: 58) | CTGTCTGCCTCTTTTGGTCAG (SEQ ID NO: 59) |
| Nos2 | GTTCTCAGCCCAACAATACAAGA (SEQ ID NO: 60) | GTGGACGGGTCGATGTCAC (SEQ ID NO: 61) |
| F4/80 | CCCCAGTGTCCTTACAGAGTG (SEQ ID NO: 62) | GTGCCCAGAGTGGATGTCT (SEQ ID NO: 63) |
| Mgl2 | GCATGAAGGCAGCTGCTATTGGTT (SEQ ID NO: 64) | TAGGCCCATCCAGCTAAGCACATT (SEQ ID NO: 65) |
| Cd206 | CTCTGTTCAGCTATTGGACGC (SEQ ID NO: 66) | CGGAATTTCTGGGATTCAGCTTC (SEQ ID NO: 67) |
| Il-10 | GCTCTTACTGACTGGCATGAG (SEQ ID NO: 68) | CGCAGCTCTAGGAGCATGTG (SEQ ID NO: 69) |
| Arg1 | CTCCAAGCCAAAGTCCTTAGAG (SEQ ID NO: 70) | AGGAGCTGTCATTAGGGACATC (SEQ ID NO: 71) |
| Cd68 | TTCTGCTGTGGAAATGCAAG (SEQ ID NO: 72) | CAATGATGAGAGGCAGCAAG (SEQ ID NO: 73) |
| Retnl | CCAATCCAGCTAACTATCCCTCC (SEQ ID NO: 74) | ACCCAGTAGCAGTCATCCCA (SEQ ID NO: 75) |
| Mcad | GTGCCCAGAGTGGATGTCT (SEQ ID NO: 76) | CCCCGCTTTTGTCATATTCCG (SEQ ID NO: 77) |

Statistical Analysis

Comparisons between two groups of data were performed using two-tailed Student's t-tests with 95% confidence intervals and ANOVA tests were used to make comparisons involving more than two groups. Values were considered to be statistically significant at p<0.05. For all data, * represents p<0.05,  represents p<0.01, and * represents p<0.005. All data are presented as mean±standard error of the mean (SEM).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and

The invention claimed is:

1. A method of treating fatty liver disease in a subject on a low fat diet comprising the step of administering to the subject an effective amount of an agent that increases the amount of C1q/TNF-Related Protein-1 (CTRP1) in the subject, wherein the agent is a recombinant CTRP1.

* * * * *